United States Patent [19]

Howard

[11] Patent Number: 5,060,656
[45] Date of Patent: Oct. 29, 1991

[54] METABOLIC RATE ANALYZER

[75] Inventor: Charles P. Howard, Ann Arbor, Mich.

[73] Assignee: AeroSport, Inc., Ann Arbor, Mich.

[21] Appl. No.: 527,106

[22] Filed: May 22, 1990

[51] Int. Cl.$^5$ ............................................. A61B 5/083
[52] U.S. Cl. ..................................... 128/718; 128/719
[58] Field of Search ................... 55/16; 128/716, 718, 128/719; 73/23.3, 31.07

[56] References Cited

U.S. PATENT DOCUMENTS

| | | | |
|---|---|---|---|
| 3,035,569 | 5/1962 | Dubsky et al. | 128/719 |
| 3,060,377 | 9/1961 | Tolbert | 128/719 |
| 3,250,270 | 5/1966 | Bloom . | |
| 3,401,683 | 9/1968 | Webb et al. | 128/718 |
| 3,799,149 | 3/1974 | Rummel et al. | 128/718 |
| 3,811,319 | 5/1974 | Arnold | 73/31.07 |
| 3,895,630 | 7/1975 | Bachman | 128/719 |
| 4,297,871 | 11/1981 | Wright | 128/719 |
| 4,368,740 | 1/1983 | Binder | 128/718 |
| 4,546,778 | 10/1985 | Sullivan | 128/718 |
| 4,549,553 | 10/1985 | Hochberg | 128/718 |
| 4,572,208 | 2/1986 | Cutler et al. | 128/719 |
| 4,619,269 | 10/1986 | Cutler et al. | 128/718 |
| 4,649,027 | 7/1987 | Talbot | 128/719 |

OTHER PUBLICATIONS

GE publication entitled, "Membrane Products" by Membrane Products Operation Medical Systems Business Operations, Mar. 1982.

Primary Examiner—William E. Kamm
Assistant Examiner—Robert L. Nasser, Jr.
Attorney, Agent, or Firm—Michael A. Mohr

[57] ABSTRACT

The metabolic rate analyzer comprises a flow proportioning valve for producing a proportional sample of the expired gas of the subject being studied. A sample cylinder is provided for drawing a proportional sample of the expired gas of the subject being studied from the flow proportioning valve. A test chamber is provided and an $O_2$ sensor is provided. The test chamber is provided with a selectively-permeable membrane, the selectively-permeable membrane having a selective permeability for $CO_2$, whereby $CO_2$ is selectively vented from the test chamber. The sample cylinder is also used for chrging the test chamber with the proportional sample of the expired gas of the subject. A pressure sensor is provided for monitoring the pressure of the sample and determining the rate of pressure decay in the test chamber due to the selective venting of $CO_2$ through the permeable membrane. An analyzing means is provided fo determining $CO_2$ content in the expired gas from the rate of pressure decay in the test chamber, conducting a volumetric analysis of the proportional sample to determine total volume of expired gas, and then correlating $O_2$ content, $CO_2$ content and total volume of expired gas to provide a measure of the metabolic rate of the subject being studied.

57 Claims, 11 Drawing Sheets

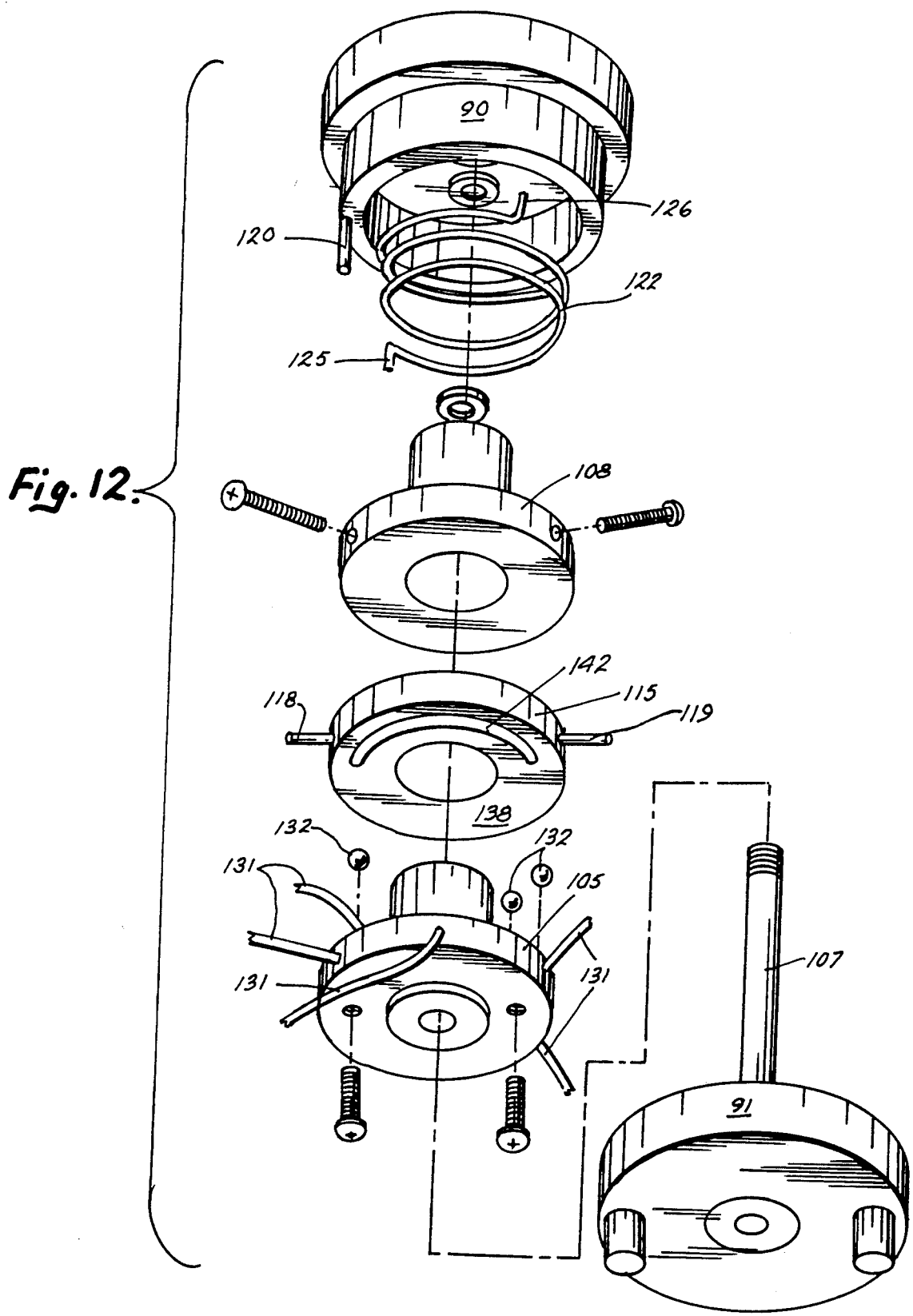

METABOLIC RATE ANALYZER

BACKGROUND OF THE INVENTION

1. Field of the Invention

The invention relates generally to the art of gas analysis and more particularly is directed to a new metabolic rate analyzer.

2. Description of the Prior Art

There are many different techniques for gas analysis in the prior art. In the field of metabolic rate analysis, various gas analysis techniques are used to measure the amount of oxygen ($O_2$) and carbon dioxide $CO_2$) in the mixture of gases inspired and expired by the subject being studied. Such techniques are used by physicians for clinical reasons and by athletes and coaches to measure fitness levels.

It has long been known that the analysis of a subject's respiratory air provides valuable information relating to the physical condition of the subject. The four most commonly-measured variables are respiratory volume, oxygen consumption, carbon dioxide production and respiratory exchange ratio (RQ), which is the ratio of carbon dioxide produced to oxygen consumed. The earliest efforts to conduct metabolic rate analysis involved the use of a so-called Douglas bag. The Douglas bag metabolic analysis technique involved the timed collection of expired breath in a rubberized breathing bag, measuring the volume of expired gas collected and analyzing the gas composition contained within the rubberized bag for $O_2$ and $CO_2$ content. Metabolic rates were then calculated from the data obtained. The Douglas bag technique was time consuming, subject to error and could only be performed on relatively stationary subjects in well-equipped laboratories. Also this technique was not well-suited to the measurement of short duration transients in metabolic functions.

Since the data obtained from respiratory gas analysis is so valuable in diagnosing cardiopulminary dysfunction and evaluating overall cardiovascular fitness, intense effort has been directed towards the development of simpler, faster, automated metabolic rate analyzers. The intense interest in physical fitness and aerobic exercise, such as running, has helped to focus further effort in this field. Many instruments are presently available for the determination of the total volume of expired air from a subject being studied. These devices include, for example, spirometers, plethysmographs and pneumotachographs. Numerous instruments are also available for determining $O_2$ content and $CO_2$ content in expired gas. Some of the more recent techniques found in the prior art involve the use of a discrete zirconium oxide $O_2$ sensor and a non-dispersive infrared (IR) gas analyzer for determining $CO_2$ content. Such instruments are accurate, however they require frequent calibration and special operating skills. Moreover, such prior art devices, especially those that provide accurate results, are costly and cumbersome. Normally, such instruments can only be used in a clinical or laboratory environment with a subject that is in a resting, or basal, condition or a subject that is confined to a stationary exercise device, such as a treadmill or stationary bicycle. Despite the intense interest now in physical fitness, there seem to be no instruments for determining metabolic rate that may be taken with an athlete, such as a runner or bicyclist, for the purpose of providing a measure of metabolic rate under conditions while the athlete is engaged in his normal exercise regime.

Measurement of metabolic rate is also useful in critically ill patients for the purpose of providing an indication f relative changes in cardiovascular function, or such other physical characteristics as tissue profusion.

Separate from the measurement of metabolic rate, $CO_2$ analysis in the expired gases of an anesthetized patient has evolved into a recognized technique for monitoring the viability of the anesthetized patient. Such $CO_2$ analyzers and gas analysis techniques relate generally to the art of capnography. The more recent capnography instruments conduct breath-by-breath $CO_2$ analysis in the end tidal gases expired from an anesthetized patient with a non-dispersive IR gas analysis technique.

Non-dispersive IR gas analysis is also the technique for $CO_2$ analysis preferred in the most recent metabolic rate analyzers. Non-dispersive IR gas analysis involves the application of infrared energy to a sample of the expired gas and the measurement of IR attenuation in the sample due to absorption of infrared energy by $CO_2$. The infrared energy applied to the same is confined to a narrow bandwidth in which it is known that $CO_2$ has a high absorptivity for infrared energy and attenuation in the sample must be compared to a reference While these instruments are portable in the sense that hey can be carried from place to place, they are relatively expensive and bulky and they have substantial power requirements which make them unsuitable for use, for example, by an athlete during his regular training regime or by a cardiac patient during rehabilitative therapy.

Another problem encountered in prior art techniques for metabolic rate analysis and $CO_2$ gas analysis involves the presence of water vapor in the expired gas. Gaseous samples of inspired air typically have a water vapor partial pressure of about zero to twenty-five torr. Moreover, in patients receiving ventilatory support in which the inspired gas is humidified, the water vapor pressure typically varies between zero and about forty-seven torr. Gaseous samples of a patient's expired gas typically have water vapor partial pressure of about forty-seven torr. Water vapor interferes with the operation of many gas analysis techniques used in the prior art, thus requiring that water vapor in the sample be minimized or removed. In doing so, errors can result from the concentrating effect of the gases being measured. Detrimental effects of water vapor on respiratory gas analysis stem from the fact that the partial pressure of the water displaces the analyzed inspired or expired gas, introducing inaccuracy. Another associated problem is the error introduced if the water vapor concentration in the inspired gas is not equivalent to the water vapor concentration in the expired gas. Equalization is often required to cancel out the affects of water vapor when the $O_2$ or $CO_2$ concentrations of the inspired and expired gases are compared. Techniques used in the prior art to remove water vapor from the sample gases, such as physically drying the gases, introduce other problems related to the condition and efficacy of the desiccating agents and the volume of the desiccator which provides increased dead space within the system and results in a longer sample time or wash-out time for measuring changes in gaseous composition.

The concept of using permeable membranes for the separation of gases and vapors dates to the nineteenth century. This technique is based on the selective permeability of certain organic materials. The term "selective permeability" as it is generally used in the art means that one gas in a mixture of gases will permeate through a membrane faster than the other gases in the mixture. It should be understood, however, that the term "selective" does not necessarily imply the passage of one gas to the complete exclusion of others. The result is always that a gas mixture on the high pressure side of the membrane is depleted in the concentration of the more permeable component, just as the gas mixture on the low pressure side of the membrane is enriched in the more permeable component. It will be apparent from the description of the present invention that, as used herein, the term "selective permeability" does not require that the gas of interest in a mixture of gases will permeate faster than the other gases in the mixture, it only requires that a significant rate of permeability is present for the gas of interest.

In selective permeable membranes, gas dissolves in the membrane on the side having a high partial pressure, diffuses through the membrane under the influence of the pressure difference, then comes out of solution on the low pressure side. This mechanism can result in large differences in permeation rates for the same gas through different polymeric membranes and a considerable spread in permeabilities for different gases in a given polymer. It has been known for some time that dimethyl silicone and many other silicone derivatives have oxygen or carbon dioxide permeabilities considerably higher than most permeable non-silicone plastics. This rapid transport is thought to be a result of the very flexible silicone-oxygen-silicone chain in the absence of crystallinity in silicone rubber. In addition to providing high permeability, such silicone membranes also demonstrate high separation factors for different types of gases, i.e., ratio of permeabilities.

Since the transport of gas or vapor, including water vapor, depends only on the partial pressure difference of the gas or vapor across the membrane, it is known that transport of a given gas or vapor, such as water, can be blocked by saturating the low pressure side of the membrane with the gas or vapor. For example, if one side of the membrane is in contact with liquid water, there will be no partial pressure driving force across the membrane, and water will not be transferred across the membrane.

Such selectively-permeable membranes have found many uses in the prior art. These include heart/lung machines where the membranes are used to separate blood from oxygen, separation and enrichment of gases such as to produce enriched air in an oxygen tent for emphysema therapy, air supply systems for space craft, underwater craft or divers, wound dressings and other barriers for passing certain gases but also filtering bacteria, pollen, dust and other contaminants, as well as in the instrumentation for gas analysis. In the instrumentation for gas analysis, such selectively-permeable membranes have been used to contact blood and other liquids for the purpose of measuring carbon dioxide levels in the liquids. In such cases, the $CO_2$ diffuses through the membrane and is then swept or purged into an instrument for conducting $CO_2$ analysis. Such selectively-permeable membranes have also been used in oxygen analyzers; for example, in enriching feed streams to gas chromatographs, and in controlling the feed streams to mass spectrometers.

SUMMARY OF THE INVENTION

According to the present invention, many of the problems in the prior art are solved by provision of a new gas analyzer and method of gas analysis employing selectively-permeable membranes which is particularly adapted to metabolic rate analysis. In a metabolic rate analyzer constructed according to the present invention, a flow proportioning valve is provided for producing a proportional sample of the expired gas of the subject being studied. The flow proportioning valve comprises a pintle valve actuated by a diaphragm which is displaced by the expired gas of the subject. A sample cylinder and sample piston are provide for drawing a proportional sample of the expired gas from the flow proportioning valve. A test chamber is provided, a discrete $O_2$ sensor is provided and the test chamber is provided with a selectively-permeable membrane, the membrane being provided with a selective permeability for $CO_2$. The membrane is disposed in the test chamber for selectively venting $CO_2$ from the test chamber. The sample cylinder and sample piston are used to charge the test chamber with the proportional sample of the expired gas of the subject, and a pressure sensor is provided for monitoring the pressure of the sample during the sample draw and when the test chamber is charged. The pressure sensor is also used to monitor the rate of pressure decay in the test chamber due to the selected venting of $CO_2$ through the selectively-permeable membrane. An analyzing means comprising a digital processor is provided for determining the $CO_2$ content of the sample from the rate of pressure decay in the test chamber; for conducting a volumetric analysis of the sample to determine the total volume of the gas expired from the subject; correlating $O_2$ content, $CO_2$ content and total volume of expired gas to provide a measure of the metabolic rate of the subject studied; and for calculating other physiological parameters of interest according to the application. A discrete temperature sensor may also be provided for monitoring the temperature of the sample and temperature correcting the analysis. It has been shown that a metabolic rate analyzer using this analysis technique or method can be embodied in a small physical package capable of being hand-held or strapped to an individual with a belt, the entire instrument weighing a few pounds or less. The power requirements of the instrument can be met with a small dry cell battery and it is believed that the instrument can be used and mounted on the body of the user much like portable radios and/or cassette players that are used by present-day athletes during their training regime. Despite the portability, convenience and inexpensive nature of this new instrument, tests have shown that it is potentially accurate for a wide range of uses, both fixed and portable, including metabolic rate measurement in a clinical setting, in a wide variety of exercise and fitness applications, in cardiac rehabilitation, and in other applications for gas analysis.

While relatively small and inexpensive discrete oxygen sensors are available, and normally in a metabolic rate analyzer such a discrete sensor is preferred, according to another aspect of the invention, a multiple gas analysis may be provided by provision of a second test chamber with a second membrane for venting a second gas of interest. Normally, different references are used external to each chamber to achieve differential permeability for the second gas of interest. According to another aspect of the invention, in the metabolic rate analyzer of the present invention, transport of water vapor (in the expired gas of the subject being studied) through the silicone rubber membrane is eliminated by a well on the low pressure side of the membrane, the well being filled with a matrix that is saturated with water to block the partial pressure driving force of water vapor across the selectively-permeable membrane.

BRIEF DESCRIPTION OF THE DRAWINGS

FIG. 12 is an exploded assembly of a crank shaft and sequencing valve assembly of the present invention;

DESCRIPTION OF THE PREFERRED EMBODIMENTS

Figure 1:
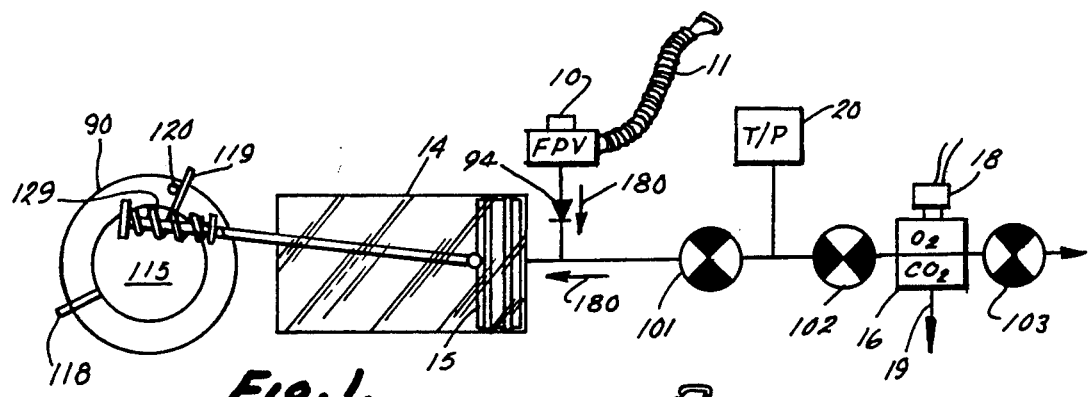
FIG. 1 is a schematic illustration of a metabolic rate analyzer constructed according to the present invention with the system poised for a sample draw.
Figure 9:
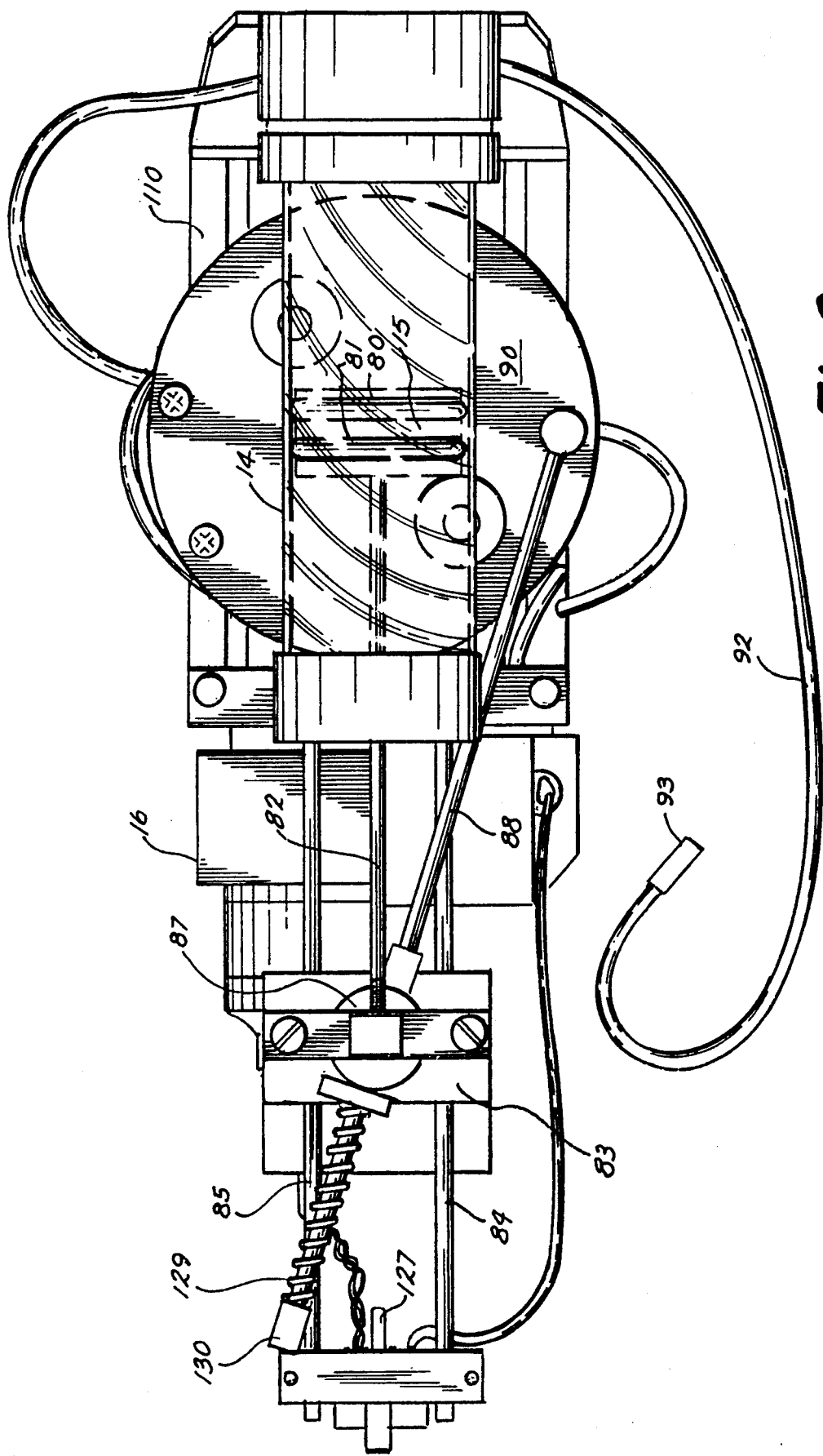
FIG. 9 is a side elevation view of the sample cylinder, connecting rods, crank shaft and test chamber of the present invention.
Figure 10:
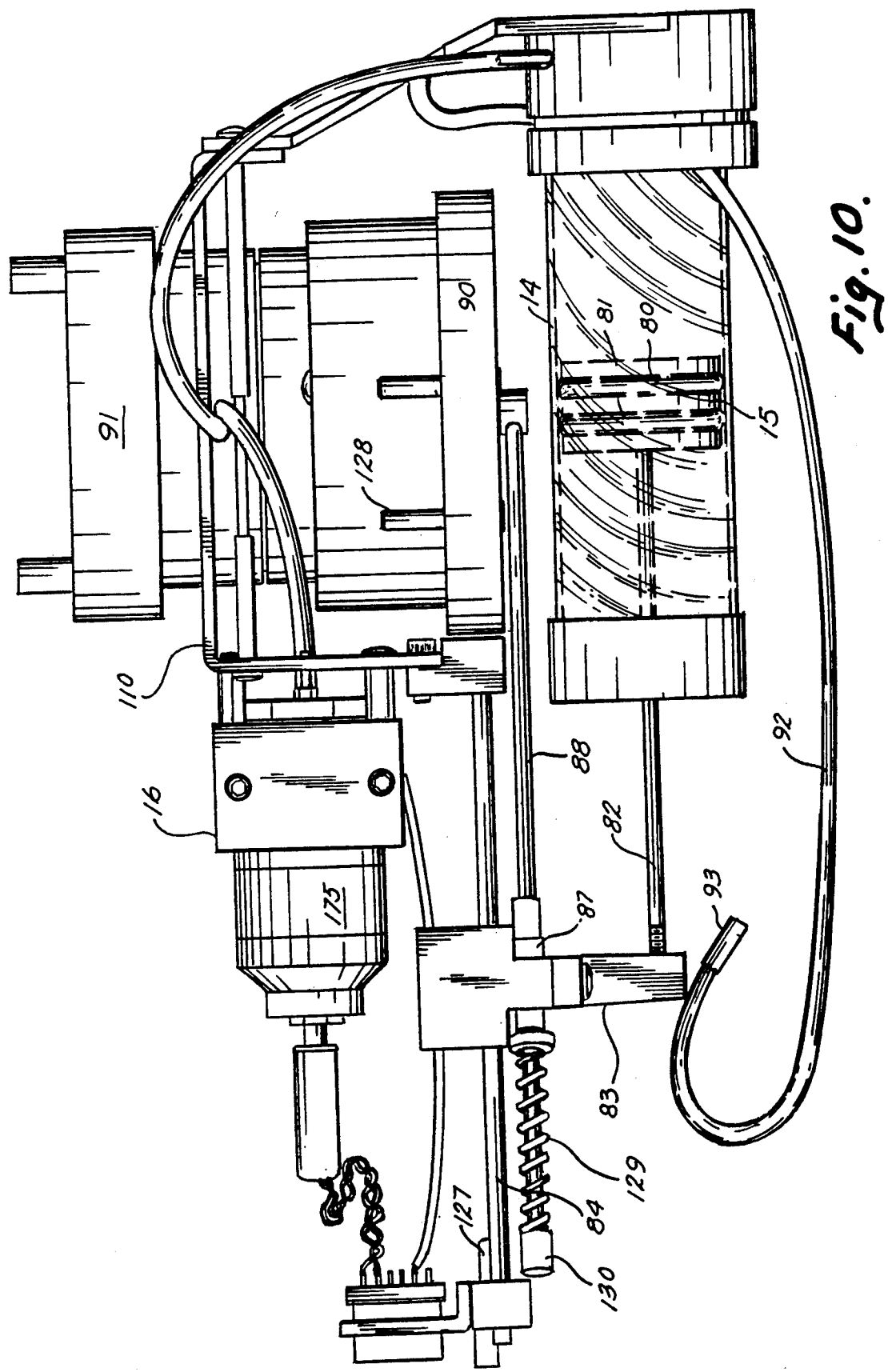
FIG. 10 is a top plan view of the mechanical assembly of FIG. 9.
Figure 11:
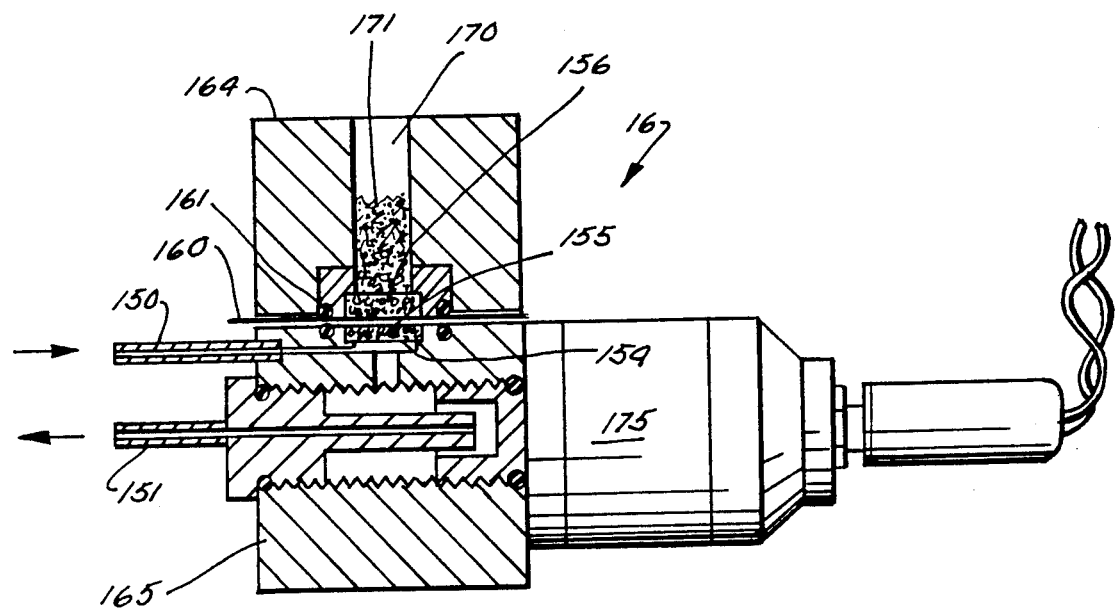
FIG. 11 is a side elevation view partially in section of the test chamber of the present invention.

With reference now to the Figures, and in particular to FIG. 1, a schematic illustration of the metabolic rate analyzer of the present invention is provided. In FIG. 1, the analyzer is illustrated poised to start a sample draw. The metabolic rate analyzer comprises a flow proportioning valve 10 for producing a proportional sample of the expired gas of a subject being studied. The flow proportioning valve 10 and components thereof are separately illustrated in further detail in FIGS. 6, 7, and 8. The subject or individual being studied provides expired gas for analysis through, for example, the mouthpiece and hose illustrated at 11. A means is provided for drawing a proportional sample of the expired gas of the subject from the flow proportioning valve comprising a sample cylinder and a sample piston illustrated at 14 and 15, respectively. The sample cylinder 14 and the sample piston 15 are best illustrated in FIGS. 9 and 10. The sample cylinder and sample piston also comprise a means for charging a test chamber illustrated at 16. The test chamber 16 is best illustrated in FIG. 11. When the sample piston is drawn from the sample cylinder, a vacuum is created for drawing a sample from the flow proportioning valve 10 and when the sample piston 15 is reversed and pushed into the sample cylinder 14, the sample contained therein is pressurized and charged into the test chamber 16. In the preferred embodiment, the test chamber 16 includes a discrete $O_2$ sensor 18 which comprises a galvanic oxygen sensor. The test chamber 16 is provided with a selectively-permeable membrane not illustrated in FIG. 1, the membrane being provided with a selective permeability for $CO_2$. The membrane is disposed in the test chamber 16 for selectively venting $CO_2$ from the test chamber 16 as schematically illustrated by the arrow at 19. Temperature and pressure sensors are disposed at 20 for monitoring the pressure of the sample during the sample draw. The temperature and pressure sensor 20 is also used to monitor during the sample charge of the test chamber and thereafter is used for monitoring the rate of pressure decay in the test chamber 16 due to the venting of $CO_2$ through the selectively-permeable membrane. An analyzer means, such as a digital processor, not illustrated in FIG. 1, determines the $CO_2$ content of the expired gas of the subject from the rate of pressure decay in the test chamber; conducts a volumetric analysis of the proportional sample from temperature, pressure and other physical constants known about the system to determine the total volume of gas expired from the subject being studied; and correlates $O_2$ content, $CO_2$ content and total volume of expired gas to provide a measure of the metabolic rate of the subject being studied.

In alternative embodiments of the invention, the temperature and pressure sensors schematically illustrated at 20 in FIG. 1 may comprise only a pressure transducer for when small temperature differentials are experienced due to small changes in pressure or other means are provided for keeping the sample at a constant temperature, it is not necessary to correct the analyzer for sample temperature.

Figure 5:
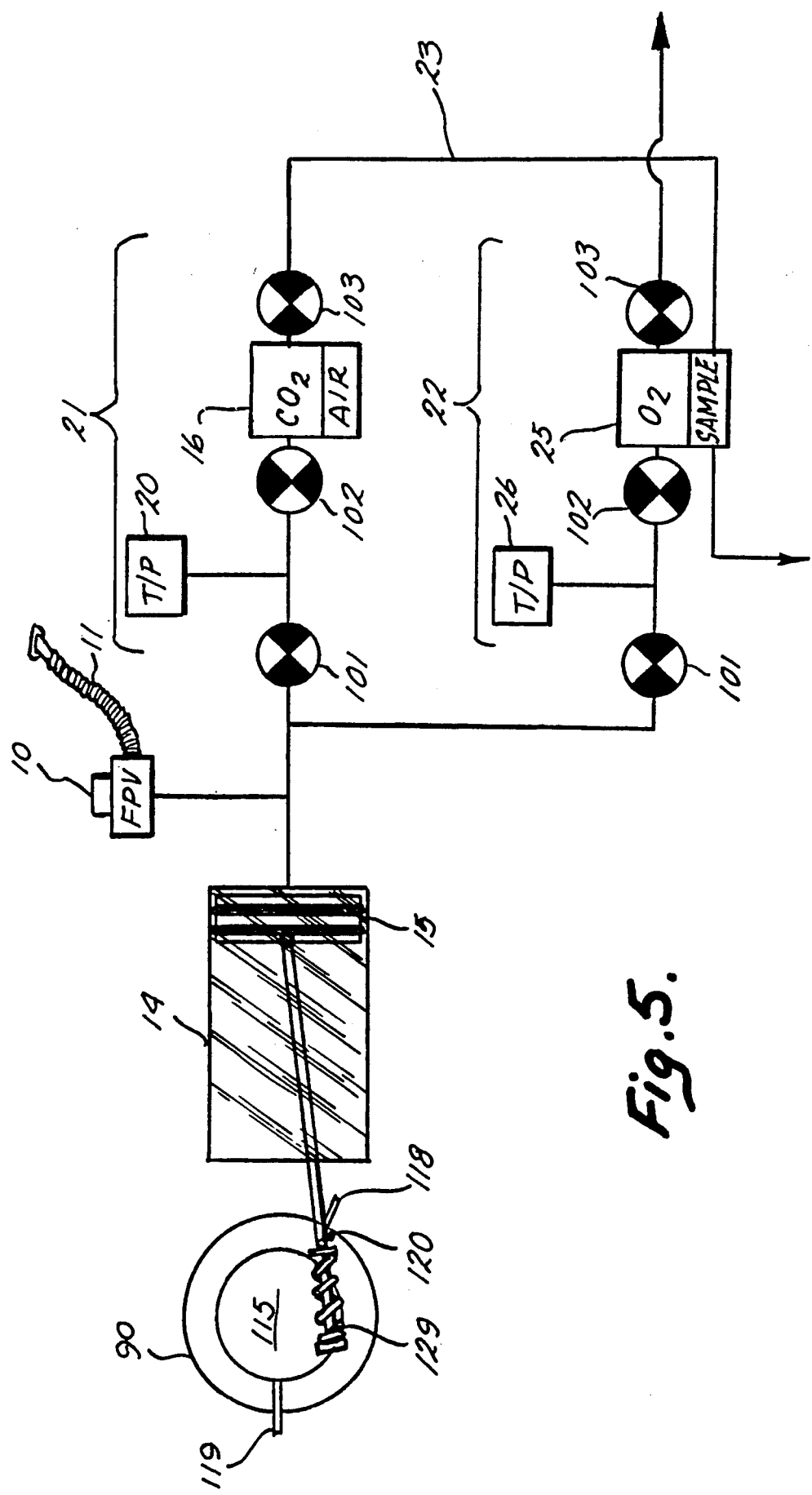
FIG. 5 is a schematic illustration of an alternative embodiment of the gas analyzer of the present invention wherein multiple gas analysis is performed with multiple test chambers and multiple membranes having selective permeability for different gases of interest.

While in the preferred embodiment of the metabolic rate analyzer of the present invention a discrete $O_2$ sensor is used because of the compact size and inexpensive nature of such transducers, FIG. 5 illustrates an alternative embodiment of the invention wherein multiple gas analysis is performed with two similar membranes with different reference gases. For example, such multiple gas analysis may take place in parallel analyzing streams or paths such as those illustrated generally at 21 for conducting $CO_2$ gas analysis and 22 for conducting $O_2$ gas analysis. In the case where a second analyzing path 22 is provided for conducting $O_2$ gas analysis, a separate $O_2$ test chamber is provided at 25 with a separate temperature and pressure transducers at 26.

A second selectively-permeable membrane disposed in the second test chamber 25 is provided with a selective permeability for venting $O_2$ from the second test chamber 25. While it may be possible to provide dissimilar membranes with selective permeabilities for $CO_2$ and $O_2$ that have similar time constants, this difficulty is overcome in the present embodiment of the invention by providing similar membranes and a different reference gas. In this case the $CO_2$ test chamber 16 is provided with a reference gas of ambient air while line 23, extending from first analyzing path 21 to second analyzing path 22, provides a reference gas of sample gas. As used herein, reference gas in each case refers to the gas disposed on the low pressure side of the selectively-permeable membrane.

The second test chamber 25 is charged with a sample of the expired gas of the subject by the sample cylinder 14 and sample piston 15 at the same time that the $CO_2$ test chamber 16 is charged. An analyzing means is provided for also determining the rate of pressure decay in the second test chamber 25 due to venting of $O_2$ through the second selectively-permeable membrane at a different rate because of the different reference gas. A set of simultaneous equations are solved by the analyzer to solve for $O_2$ content from the different pressure decay rates in test chamber 16, and test chamber 25 due to the presence of different reference gases of air and sample gas, respectively.

Figure 6:
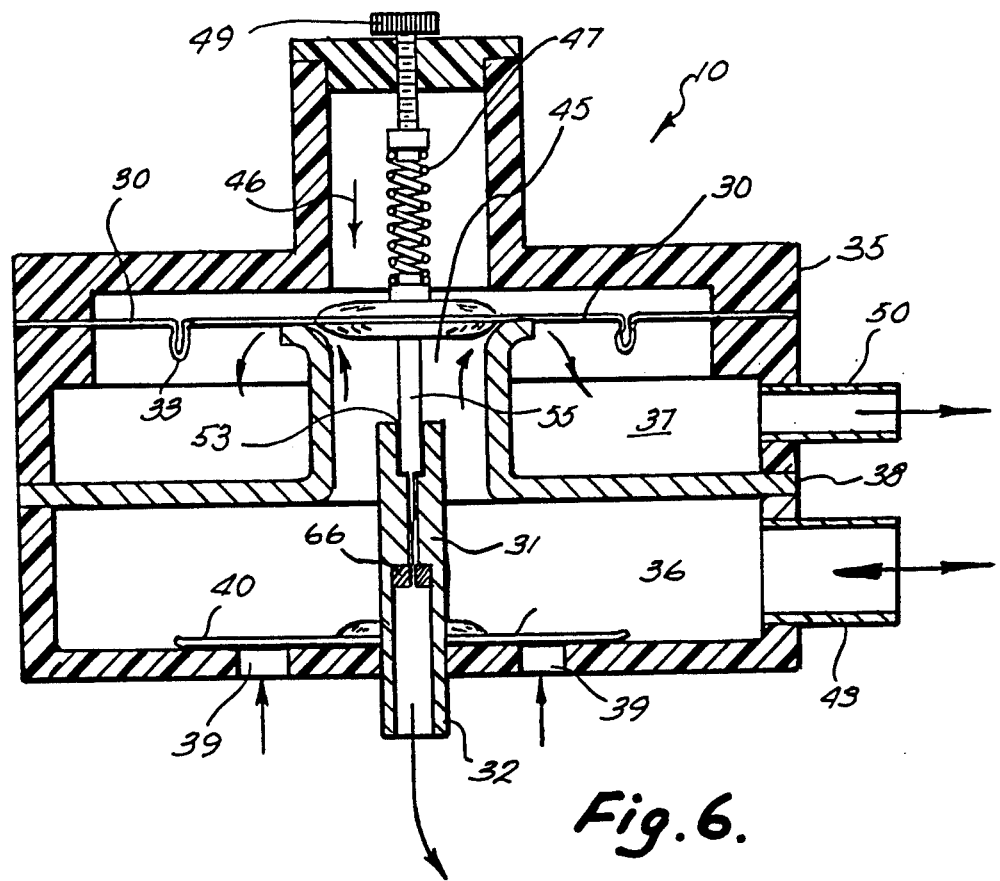
FIG. 6 is an elevation view partially in section of the flow proportioning valve of the present invention.

With particular reference now to FIG. 6, the flow proportioning valve 10 is illustrated in further detail. The flow proportioning valve 10 comprises a diaphragm 30 which is actuated by the expired gas of the subject being studied. A pintle valve disposed at 31 is connected to the diaphragm 30 and is actuated proportionally by the displacement of the diaphragm 30. The output of the pintle valve 31 at sample outlet port 32 is connected to the sample cylinder and sample piston which draws the proportional sample from the flow proportioning valve. The diaphragm 30 is a flexible, rubberized fabric or web which may contain one or more pleats 33 to increase its flexibility. A highly flexible membrane 30 is desirable to minimize the back pressure felt by the subject when respiratory gases are expired into the flow proportioning valve. The diaphragm 30 is suspended in a valve housing 35 that is bifurcated into an inlet manifold 36 and an outlet manifold 37 by a manifold wall 38. The inlet manifold 36 is provided with a plurality of inlet apertures 39 covered by a one-way flap valve 40 for admitting inspired air only through the inlet apertures 39 in the inlet manifold 36. The inlet manifold 36 also comprises a breath port 43 through which the subject receives inspired air and discharges expired gas. The mouthpiece and hose referred to above and illustrated at 11 in FIG. 1 are normally connected to breath port 43. The manifold wall 38 further comprises a gas outlet port 45 which is normally covered and closed by the flexible diaphragm 30. The flexible diaphragm 30 is spring biased in the direction of the arrow 46 toward the expired gas outlet port 45 by a compression loaded coil spring 47 mounted between the flexible diaphragm 30 and a manually-adjustable thumb screw 49. The force provided by the compression spring 47 is not great because any substantial spring bias would significantly increase the back pressure felt by the subject being studied as air is expired into the flow proportioning valve. Thus, the spring tension is set at a value just sufficient to prevent the flexible diaphragm 30 from being accidentally displaced due to movement of the flow proportioning valve 10 during vigorous exercise, such as running. The outlet manifold 37 further comprises a main outlet port 50 for expired gas. However, a proportional flow of expired gas also exits the flow proportioning valve from the sample port 32 through pintle valve 31 which is actuated by flexible diaphragm 30.

The inlet 53 for the pintle valve 31 is disposed in the inlet manifold 36 of the flow proportioning valve 10. In the operation of the flow proportioning valve 10, expired air is discharged into the inlet manifold 36 through the breath port 43. The flap valve 40 covers inspired air ports 39 so that the only outlet port 45 which is normally covered and closed by the flexible diaphragm 30. Pressure from the the expired outlet port 45 which is normally covered and closed by the flexible diaphragm 30. Pressure from the expired gas in the inlet manifold 36 thus compresses the spring 47, lifting the flexible diaphragm 30 to permit the escape of expired air through the expired gas outlet port 45 into the outlet manifold 37. The main expired gas flow then continues through the expired main outlet port 50. The pintle valve 31 is connected to the flexible diaphragm 30 by a central shaft 55 linking the same. The central shaft 55 extends through the center of the inlet port 53 of the pintle valve 31 to actuate the same proportionally with the displacement of the flexible diaphragm 30. Since the flexible diaphragm 30 is displaced proportionally with the volume of expired gas directed through the expired gas outlet port 45, the pintle valve is thus directly and proportionally actuated by the displacement of flexible diaphragm 30 and the total volume of expired air. A small proportional sample of the expired air is thus drawn from the sample port 32 of the flow proportioning valve 10 by the vacuum created in the sample cylinder 14 when the sample 15 is withdrawn from the sample cylinder.

Figure 7:
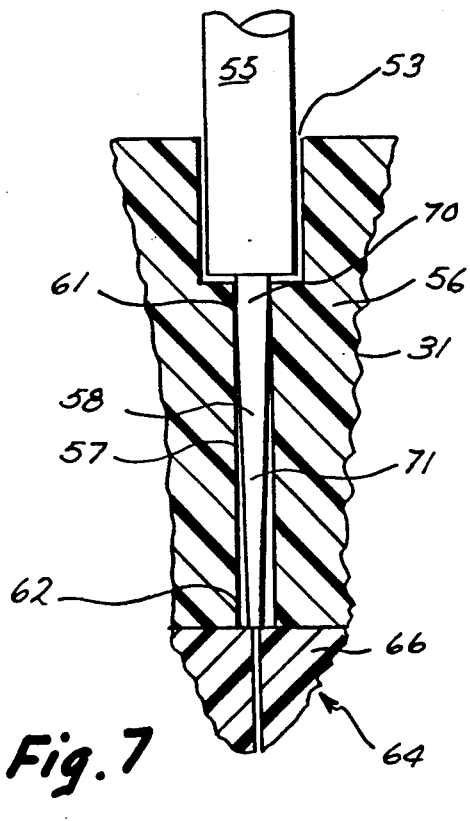
FIG. 7 is a partial elevation partially in section of the pintle valve of the present invention.
Figure 8:
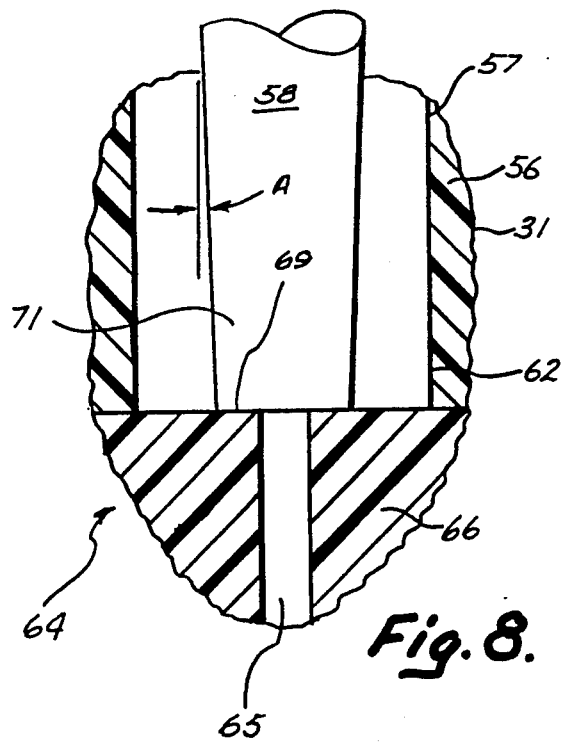
FIG. 8 is a partial view partially in section of the shut-off valve comprising a portion of the pintle valve of the present invention.

With reference also to FIGS. 7 and 8, the pintle valve 31 is illustrated in further detail. The pintle valve 31 comprises a valve body 56, a generally cylindrical bore 57 disposed in the valve body 56 and a needle-shaped valve spindle 58 generally cylindrical in cross section, disposed in the cylindrical bore 57. The cylindrical bore 57 is provided with proximate end 61 and a distal end 62. The valve spindle 58 is inserted in the proximate end 61 of the cylindrical bore 57 and extends colinearly with the central axis of the cylindrical bore 57.

As best illustrated in FIG. 8, the pintle valve further comprises a positive shut-off valve generally illustrated at 64. The positive shut-off valve comprises an output passage 65 disposed in the distal end 62 of the cylindrical bore 57. The output passage 65 is in fluid communication with sample port 32 of the flow proportioning valve 10 and is disposed in elastomer seat 66, covering the distal end 62 of the cylindrical bore 57. The elastomer seat 66 may, for example, be formed from an elastomer identified by the trademark Viton and available from DuPont. The valve spindle 58 is normally formed from stainless steel. The elastomeric seat thus surrounds the output passage 65 and is engaged by a blunt sealing surface 69 disposed on the end of the needle-shaped valve spindle 58. The compression spring 47 illustrated in FIG. 6 provides sufficient clamping force to urge the blunt sealing surface 69 of the needle-shaped valve spindle 58 into clamping engagement with the elastomer seat 66 to provide a positive shut-off for the pintle valve. Since only very small clamping pressure are provided by the spring 47 for the purpose of reducing back pressure in the system, and very small sample flows are metered through the output passage 65, this shut-off valve geometry has several advantages. The diameter of the output port 65 is approximately 0.040 inch. The diameter of the blunt sealing surface 69 of the needle-shaped valve spindle 58 is approximately 0.066 inch. The needle-shaped valve spindle 58 is formed from stainless steel. The small contact area between the stainless steel blunt sealing surface 69 and the viton seat 66 thus provides a very precise positive flow shut-off for very small sample flows while minimizing valve stiction.

With reference now also again to FIG. 7, it is illustrated that said cylindrical bore 57 is provided with a right circular cross section which is constant throughout its length. The needle-shaped valve spindle 58 is provided with a guide portion 70 of right circular cross section that is slightly smaller than the right circular cross section of said bore, whereby a sliding fit is established between the bore and the cylindrical guide portion 70 of the spindle 58. The spindle 58 is further provided with a meter portion 71 of conical cross section. The meter portion 71 is disposed between the guide portion 70 and the blunt sealing surface 69 of the needle-shaped valve spindle 58. The meter portion of the spindle 58 is provided with a constant one-half degree taper, illustrated by the angle A in FIG. 8, along the entire length of its conical cross section. The nominal diameter of the cylindrical bore 57 in the valve body 56 of the pintle valve 31 is 0.070 inch. With the needle-shaped valve spindle 58 being provided with one-half degree taper, the blunt sealing surface 69 of the needle-shaped valve spindle 58 is provided with a diameter of approximately 0.066 inch.

Figure 14:
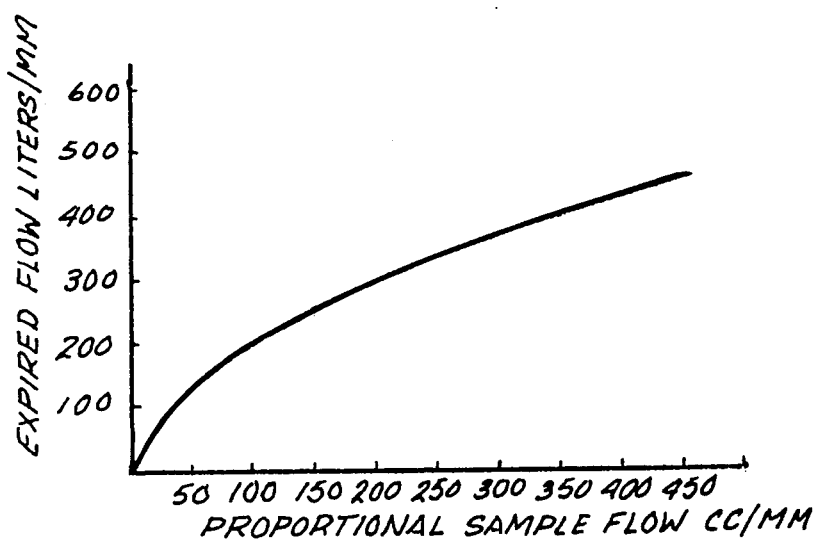
FIG. 14 is a plot of expired flow versus proportional sample flow for the flow proportioning valve of the present invention.

With reference now also to FIG. 14, the advantage of this pintle valve geometry is illustrated in a plot of expired flow in liters per minute versus proportional sample flow in cubic centimeters per minute. FIG. 14 illustrates that the relationship between total expired flow and proportional sample flow is nearly linear for any significant sample flow above fifty cubic centimeters per minute. This linearity is the result of very high Reynolds numbers for sample flows through this pintle valve geometry. Flow is not linear in beginning at low Reynolds numbers where flow is generally laminar. However, as soon as flow rates increase and turbulence increases with higher Reynolds numbers, the pintle valve geometry just illustrated produces a linear relationship between expired flow and sample flow. Since most sample flow is at flow rates much higher than fifty cubic centimeters per minute, almost no compensation is required. However, where a digital processor is used to conduct volumetric analysis, a curve fit is conducted to provide a signal representative of the actual expired flow passing through the proportional flow valve to correct for the non-linearities actually observed between sample flow and expired flow. Alternatively in applications where low expired flow ratios are often encountered, the mean diameter of the needle-shaped valve spindle 58 can be reduced that higher Reynolds numbers are attained at lower flows, thus extending the linearity to the lower range of flow rates.

With reference to FIGS. 9 and 10, the sample cylinder 14 and sample piston 15 are illustrated in further detail. The sample piston 15 is in sliding and sealing engagement with the sample cylinder 14. In the preferred embodiment, the sample cylinder 14 is formed from a cylindrical glass tube and the sample piston 15 is surrounded by a plurality of sealing, elastomer, O-rings 80 and 81 which are compressed between the glass sample cylinder 14 and the sample piston 15. For example, the O-rings may be formed from the aforementioned Viton material available from DuPont. Striction between the sample cylinder and the sample piston is thus minimized while providing a positive sealing engagement therebetween. Angular displacement of the piston 15 relative to the cylinder 14 is avoided by provision of first connecting rod 82 extending from the sample piston 5. The first connecting rod 82 is only displaced linearly along with the displacement of the sample cylinder 15. Linear displacements of the first connecting rod 82 are transmitted to a reciprocating carrier 83 which is journaled for reciprocal motion on a pair of guide rails 84 and 85. Journaled on carrier 83 is a cylindrical bushing 87 which receives a second connecting rod 88. The second connecting rod 88 reciprocates and rotates with a crank shaft wheel 90 which is actuated by hand crank 91. When proportional sample of the expired gas of the subject is to be drawn from the flow proportioning valve 10, the crank shaft wheel 90 is turned, withdrawing the sample piston 15 from the sample cylinder 14 to draw a proportional sample into the sample cylinder through a flexible tube 92 that is in flow communication with the sample port 32 of the flow proportioning valve 10. A one-way check valve 94 is schematically illustrated in FIG. 1, between the outlet port 32 of the flow proportioning valve 10 and a connection 93 on the end of flexible tube 92 to ensure that sample flow will pass in only one direction from the flow proportioning valve 10 to the sample cylinder 14. However, in the present case, no such check valve is required because the shut-off valve 64 of the flow proportioning valve 10 of the preferred embodiment is a one-way valve. The pressures generated in the sample cylinder are not sufficient to lift the needle-shaped valve spindle 58 because of the small are (0.040 inch diameter) of the output passage 65 of the shut-off valve 64. When the rotation of crank shaft wheel 90 continues, the sample piston 15 is displaced back into the sample cylinder 14 to pressurize the proportional sample and charge the test chamber 16 with the sample.

With reference now again to FIG. 1, first and second sequence valves 101 and 102 are provided for sequencing sample flow in the metabolic rate analyzer. The first sequence valve 101 interconnects the sample cylinder 14 and the temperature/pressure sensor 20. The first sequence valve 101 is open when the sample is drawn to provide for temperature and pressure monitoring during the sample draw. The first sequence valve 101 is open for directing sample to the test chamber 16 when the sample piston 15 is displaced into the sample cylinder 14 to charge the test chamber with the sample. Thereafter, the first sequence valve 101 is closed during analysis for isolating the test chamber 16 while monitoring pressure decay in the test chamber.

The second sequence valve 102 interconnects the temperature/pressure 20 and the test chamber 16, the second sequence valve 102 being closed when the sample is drawn for isolating the sample cylinder and the flow proportioning valve from the test chamber 16 during the sample draw. The second sequence valve 102 is open when the test chamber is charged for directing the sample to the test chamber. The second sequence valve remains open during analysis to provide for the monitoring of temperature and the monitoring of pressure decay in the test chamber 16. A vent valve 103 is provided for connecting the test chamber 16 to a vent. The vent valve 103 is open when the sample is drawn and the vent valve 103 is closed when the test chamber is charged. The vent valve 103 remains closed during analysis for isolating the test chamber while monitoring temperature and monitoring pressure decay in the test chamber 16.

With reference now also to FIGS. 9, 10 and 12, and with particular reference to FIG. 12, it is illustrated that the first sequence valve 101, the second sequence valve 102 and the vent valve 103 are disposed in a stationary valve assembly 105 that is disposed about the central shaft 107 of the crank shaft 90. While the crank shaft wheel 90, the hand crank 91 and a central crank shaft 107 are rotatable, the stationary valve assembly 105 is bolted to a cam cover and spring support 108, which is secured to the stationary frame or chassis 110, illustrated in FIGS. 9 and 10 of the metabolic rate analyzer. A rotary cam assembly 115 is journaled on central crank shaft 107 and includes a sample pawl 118 and a reset pawl 119 which are alternately engaged by crank shaft pawl 120 disposed on crank shaft wheel 90. The crank shaft member wheel 90 is bolted or otherwise suitably secured with a spline or the like to the central crank shaft 107 so that it turns with the hand crank 91. A torsionally loaded coil spring 122 extends about the central crank shaft 107, the coil spring having one tail 125 connected to the stationary cam cover and spring support 108, with the other tail 126 connected to the crank shaft wheel 90. Thus, in the operation of the metabolic rate analyzer of the present invention, the hand crank 91 is rotated in one direction to turn the crank shaft wheel 90, torsionally loading the coil spring 122 so that the spring 122 thereafter drives the crank shaft wheel in the other direction, withdrawing the sample piston 15 from the sample cylinder 14 during the sample draw. Once the draw is complete, the piston is prevented from further displacement toward bottom dead center by a resilient spring loaded stop or detent 127. Then, the hand crank 91 is turned manually, driving the sample piston 15 and carrier 83 through the stop 127 and allowing the crank shaft wheel to continue past bottom dead center of the sample cylinder 15, toward top dead center, compressing the sample gas contained therein and thus charging the test chamber 16. The user continues to manually turn the hand crank 91 until the hand crank hits a stop post 128, which in terms of angular position is disposed near the top dead center position of the sample piston 15, and the first sequence valve 101 is closed, thus trapping a pressurized quantity of the sample gas in the test chamber 16 at the end of the sample charge.

A mechanical arrangement for limiting and normalizing the maximum pressure achieved in the test chamber 16 during the sample charge is provided, comprising a compression loaded coil spring 129 disposed on one end of the first connecting rod 88. The coil spring 129 is compressed between the carrier 83 and a stop 130 on the end of the first connecting rod 88. The first connecting rod 88 is slidably received in cylindrical bushing 87 on reciprocating carrier 83 so that when the pre-set compression of spring 129 is overcome by pressure building up in the sample cylinder 14, further displacement of the sample piston 15 into the sample cylinder 14 is prevented by compression of spring 129 between cylindrical bushing 87 and stop 130. Thus, as the hand crank 91 is turned further toward the stop post 128, further displacement of the sample piston 15 is prevented by the sliding connection between the second connecting rod 88 relative to the carrier 83.

Figure 13:
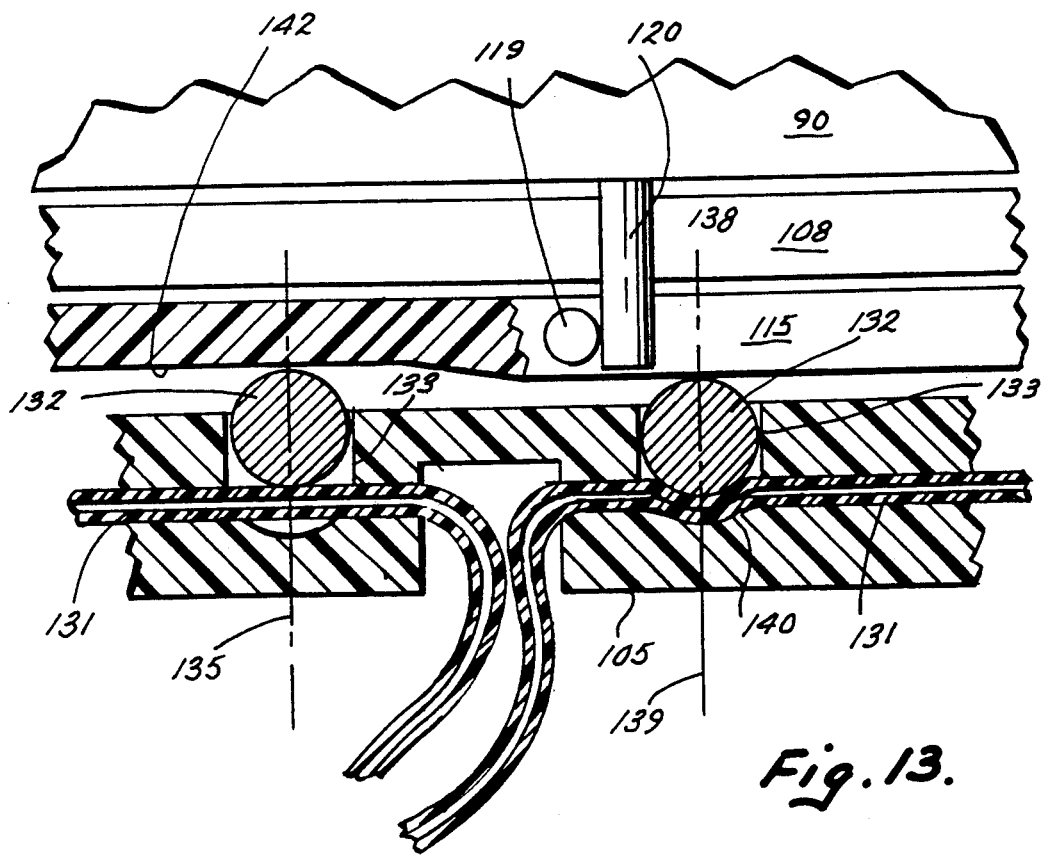
FIG. 13 is a partial elevation partially in section of the valve sequencing assembly of the present invention.

With reference now also to FIG. 13, each of the first sequence valve 101, the second sequence valve 102, and the vent valve 103 comprise a length of flexible, elastomer tubing 131 which extend through the stationary valve assembly 105. Each of these valves also comprises a ball actuator 132 which is disposed for reciprocal motion in an actuator bore 133 which extends in a direction generally orthogonal to the direction of the tubing 131. The actuator bore 133 intersects the tubing 131 so that the ball actuator 132 is in an abutting relationship with the tubing 131. Since the tubing 131 is formed from a resilient, elastomeric tubing such as a silicone rubber, normally the ball actuator is spring biased upwardly to the position illustrated at 135 in FIG. 13. However, each ball actuator 132 is provided with a dimensional relationship to the actuator bore 133 so that it normally extends above the actuator bore 133. The portion of the ball actuator extending above the actuator bore is engaged by a cam surface 138 of cam cover 115 which displaces the ball actuator downwardly into engagement with the elastomer tubing 131 and clamps the same closed and to provide a positive shut-off valve.

In FIG. 13 a ball actuator 132 is illustrated in the closed position at 139. As illustrated at 139, the cam surface 138 displaces the actuator ball 132 down into the elastomeric tubing 131 to collapse the same against a soft seat 140 disposed below the elastomer tubing 131. This arrangement provides a plurality of valves which are sequentially actuated by the rotatable cam cover 115 but which provide positive flow shut-off with minimum valve stiction.

As best illustrated in FIG. 12, the ball actuators 132 are disposed in a circular array in the stationary valve assembly 105 so that the actuators are alternately depressed by the flat surface 138 of the rotary cam assembly 115 or retracted into a circular track 142 of circular cross section, which is disposed in the cam surface 138 of the rotary cam assembly 115. Alternately driven sample pawl 118 and reset pawl 119, which are alternately engaged by crank shaft pawl 120, drive the rotary cam assembly 115 alternately one direction or the other about the central crank shaft 107 to reciprocate the ball actuators 132 and sequence the valves necessary to draw sample gas, purge the system, charge the test chamber, and analyze the sample as hereinafter described in the operation of the metabolic rate analyzer of the present invention.

With reference now to FIG. 11, the test chamber 16 is illustrated in further detail. The test chamber 16 comprises a pressure vessel having a sample inlet 150, a sample outlet 151, a sample window 154, a first porous sintered metal plate 155 disposed in the sample window 154, and a second porous sintered metal plate 156 disposed in the sample window 154. The sintered metal plates 155 and 156 are normally formed from stainless steel having a five micron pore size. A selectively-permeable membrane 160 is sandwiched between the first and second sintered metal plates 155 and 156 and is supported by the same. The selectively-permeable membrane 160 is further held in place by a plurality of O-rings 161 which surround the sample window 154. The O-rings 161 are clamped between a window block 164 and the main test chamber body 165, the clamping force being provided by fasteners not illustrated herein which bolt and clamp the window body 164 to the main body 165 of the test chamber.

According to the present invention, and particularly in the case where $CO_2$ analysis is conducted in a metabolic rate analyzer, the selectively-permeable membrane 160 is formed from a silicone rubber. In the preferred embodiment of the analyzer, $CO_2$ gas analysis and $O_2$ gas analysis is conducted with a membrane formed from dimethyl silicone available from General Electric. In the case where a silicone rubber membrane is provided, compensation for water vapor in the sample gas is provided by provision of a well 170 disposed in the window block 164 of the test chamber. The well 170 may further contain a matrix 171 of lint, cotton, or the like, which is saturated with water to keep the low pressure or vent side of the membrane 160 wet and thus block the partial pressure driving force for water vapor which would normally extend across the selectively-permeable membrane 160.

FIG. 11 also illustrates that in the preferred embodiment of the metabolic rate analyzer of the present invention a discrete $O_2$ sensor comprising a galvanic oxygen cell 175 is bolted or otherwise suitably secured with sealing O-rings or the like to the main body 165 of the test chamber to provide a measure of $O_2$ content in the sample gas contained therein. Such cells are also known in the trade as galvanic fuel cells. A galvanic oxygen cell suitable for the preferred embodiment of the present invention is available from the Catalyst Research Company.

Figure 17:
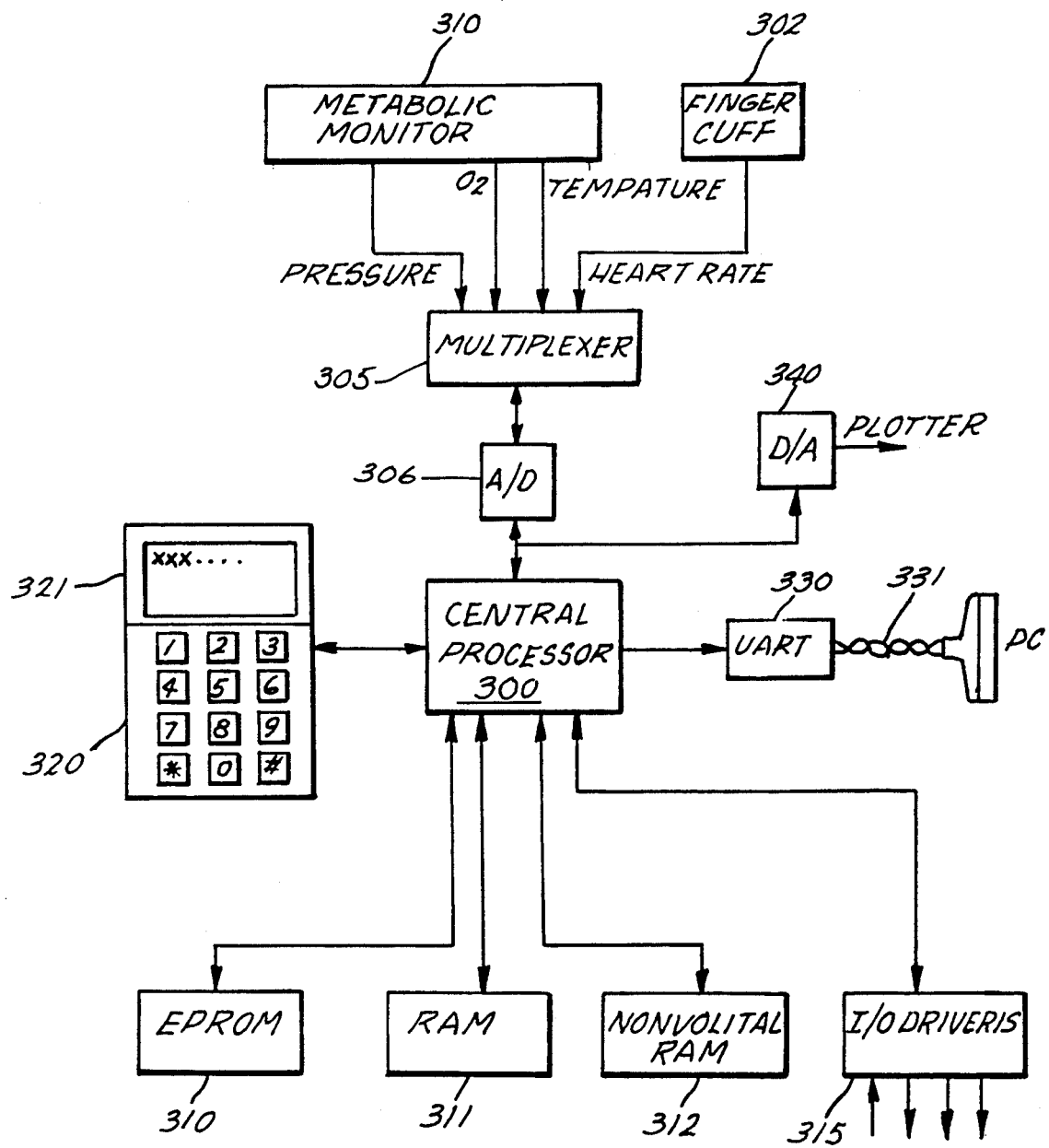
FIG. 17 is a block diagram of the processing electronics of the metabolic rate analyzer of the present invention.

With reference now to FIG. 17, the analyzing means is illustrated in block form. The analyzing means comprises a central processor 300 that receives inputs from the metabolic monitor at 301 and other devices such as the finger cuff at 302. Outputs from the metabolic monitor 301 and finger cuff 302 include pressure, $O_2$, temperature and heart rate. These analog inputs are directed to an eight channel multiplexor 305 and then a twelve bit A to D converter 306 so that the signals can be inputted to the central processor 300. The analyzer further comprises a read-only memory 310 which may, for example, comprise an EPROM where the analyzer program resides along with the look-up tables or curves. A random access memory or RAM 311 is provided for reading and writing, carrying out arithmetic functions and storing temporary data. A nonvolatile random access memory is provided at 312 for storing calibration constants and ventilation equivalents in units of volume per minute for the flow proportioning valve. The nonvolatile RAM 312 for storing ventilation equivalents may not be necessary if the flow proportioning valve can be manufactured inexpensively with a repeatable response curve. If the response curve of the flow proportioning valve is repeatable, the ventilation equivalents may be stored in the EPROM 310. Otherwise, each flow proportioning valve will be calibrated and ventilation equivalents will be stored in the nonvolatile RAM 312, which is a type of RAM storage which retains data when power is removed from the device. The analyzer further comprises digital input/output drivers 315 which may be used, for example, to drive status lights, an enunciator or the like which identifies different stages in the operation of the metabolic monitor for the user.

In the present embodiment of the invention, the analyzer also includes a keyboard 320 and a display 321 for interfacing with the user. In this case, the display 321 is a four-line by twenty character liquid crystal display and the keyboard 320 comprises a full numeric keyboard. However, in other embodiments of the invention, it may not be necessary to provide a full numeric keyboard. In some embodiments, for example, the keyboard 320 and display 321 may comprise one or two keys to sequence data on a single twenty character display line. In the present embodiment of the invention, a full keyboard is desirable for providing inputs to the central processor 300. A universal asynchronous receiver transmitter or UART is provided at 330 for communicating to an IBM compatible-type personal computer or the like through an RS-232 serial data line 331. Thus, the user can download the output of the metabolic monitor to a personal computer for the purpose of further processing or displaying, for example in graphic form, the output of the metabolic monitor. Other users may operate the metabolic monitor as a slave to a personal computer, exchanging information or issuing commands to the central processor 300 through the RS-232 link.

In the present embodiment of the invention, a digital to analog converter is also provided at 340 as a diagnostic tool. The D to A converter 340 is provided so that the user can quickly and expediently play back the pressure decay curve stored in the central processor and the two curves in RAM memory which most closely fit the actual pressure decay curve. These curves can then be inputted to an analog chart recorder to quickly confirm that a good curve fit has been provided by the central processor 300. Like the numeric keyboard 320, however, this is primarily a diagnostic and development tool which may not be provided in all embodiments of the invention.

In the operation of the analyzer illustrated in FIG. 17, signals representative of sample pressure, $O_2$ content, sample temperature and heart rate are inputted to the central processor 300 through a channel multiplexer 305 and A to D converter 306. The central processor 300 then makes a temperature correction to the gas pressure signal. When the test chamber is charged by the sample cylinder and sample piston, the central processor 300 is cued by the large spike received in the pressure signal. Thereafter, the central processor 300 analyzes the slope of the logarithmic pressure decay curve. The central processor 300 stores a value that is representative of the maximum initial charging pressure of the test chamber and then every ten milliseconds thereafter the pressure signal is sampled and stored to provide a measure of the pressure decay curve in the test chamber. This analysis continues for a number of seconds, and then the actual measured decay curve is compared by the central processor 300 to examples of decay curves stored in the RAM memory 310 for different $CO_2$ content in the sample. The processor finds the two closest curves stored in RAM memory and then conducts a linear interpolation between the curves to generate a representative value for $CO_2$ content in the sample gas. Since the volumetric ratio between the gas sample received from the flow proportioning valve and the actual volume of the gas expired by the subject being studied is known, and the time for the sample cylinder to fill is known, the central processor can determine the ventilation rate or the amount of air expired by the subject per minute. $O_2$ content in the expired gas is a direct input from the $O_2$ sensor. Therefore, the central processor, using ambient air as a reference, can calculate oxygen consumption, $CO_2$ production, volume, and respiratory quotient. The processor also provides a measure of the respiration rate by monitoring the cyclical change in the pressure signal during the sample portion of the operating cycle. Thus, the processor 300 will determine the first derivative of this cyclical pressure wave form, best illustrated between points A and B of the plot of FIG. 15, and the result will be the breath rate of the individual being studied. With these inputs, a wide variety of information can be generated by the central processor 300 and displayed, such as $O_2$ consumed per breath, the volume of each breath, etc.

Environmental factors come into play when analyzing gas volumes obtained during physiological measurements. Gas volumes obtained during physiological measurements are usually expressed in one of three ways: ambient temperature pressure saturated (ATPS), standard temperature pressure dry (STPD), or body temperature pressure saturated (BTPS). ATPS refers to the volume of gas at the specific conditions of measurement which are therefore at ambient temperature (273 degrees Kelvin plus ambient temperature in degrees Centigrade), ambient pressure and saturated with water vapor. Gas volumes collected during pulmonary function tests are initially measured at ATPS. The volume of gas, however, varies depending on its temperature, pressure and content of water vapor, even though the absolute number of gas molecules remains constant. With respect to temperature, the volume of a gas varies directly with temperature. Increasing the temperature causes the molecules to move more rapidly, expanding the gas mixture and increasing the volume proportionally (Charles' Law) In the case of pressure, the volume of the gas varies inversely with pressure, increasing the pressure forces molecules closer together, causing the volume to decrease in proportion to the increase in pressure (Boyle's Law). In the case of water vapor, the volume of a gas varies depending on its water vapor content. The volume of gas is greater when the gas is saturated with water vapor than when the same gas is dry or contains no moisture.

These factors, temperature, pressure and the relative degree of saturation of the gas with water vapor, must be considered, especially when gas volumes are compared under different environmental conditions and subsequently used in metabolic and physiologic calculations. The standards that provide the frame of reference for expressing a volume of a gas are either STPD or BTPS.

STPD refers to the volume of a gas expressed under standard conditions of temperature (273 degrees Kelvin, or zero degrees Centigrade), pressure (760 millimeters Hg) and dry (no water vapor). Expressing a gas volume, STPD for example, makes it possible to evaluate and compare the volumes of expired air measured while running in the rain at high altitude along a beach in the cold of winter or in a hot desert environment below sea level. Thus, in all metabolic calculations, gas volumes are always expressed at STPD. This and many of the other metabolic computations provided herein ar set forth in full detail in the publication entitled "Exercise Physiology" by W. D. Mcardle, F. I. Katch and V. L. Katch, published by Lea And Febiger, 1981, which is incorporated herein by reference.

To reduce a gas volume to standard temperature, the following formula is used:

$$\text{Gas volume } ST = V_{ATPS} \times \frac{273° \text{ K.}}{273° \text{ K.} + T° \text{ C.}} \quad (1)$$

where T° C. equals temperature of the gas in the measuring device and 373° K. equals absolute temperature Kelvin, which is equivalent to 0° C. This temperature correction is normally provided by the analyzer of the present invention.

Similarly, the following equation is used to express a gas volume at standard pressure (SP):

$$\text{Gas volume } SP = V_{ATPS} \times \frac{P_B}{760 \text{ mm Hg}} \quad (2)$$

where $P_B$ equals ambient barometric pressure in mm Hg and 760 equals standard barometric pressure at sea level, mm Hg.

To reduce a gas to standard dry (SD) conditions, the effects of water vapor at the particular environmental temperature must be subtracted from the volume of gas. Because expired air is generally one hundred percent saturated with water vapor, it is usually not necessary to determine its percentage saturation from measures of relative humidity. The vapor pressure in moist or completely humidified air at a particular ambient temperature can be obtained and is expressed in mm Hg. This vapor pressure ($P_{H2O}$) is then subtracted from the ambient pressure ($P_B$) to reduce the gas to standard pressure dry (SPD) as follows:

$$\text{Gas volume } SPD = V_{ATPS} \times \frac{P_B - P_{H2O}}{760} \quad (3)$$

By combining equations (1) and (3), any volume of moist air can be converted to STPD as follows:

$$\text{Gas volume } STPD = V_{ATPS} \left( \frac{273}{273 + T° \text{ C.}} \right) \left( \frac{P_B - P_{H2O}}{760} \right) \quad (4)$$

Fortunately, these computations may not have to be carried out because the appropriate STOD correction factors are already calculated for moist gas in the range of temperatures and pressures ordinarily encountered. Thus, multiplying any gas volume ATPS by the appropriate correction factor can provide the same sample gas volume STPD that would be obtained if values for the ambient temperature barometric pressure and water vapor pressure were substituted into equation (4).

The term BTPS refers to a volume of gas expressed at body temperature (usually 273 degrees Kelvin plus 37 degrees Centigrade, or 310 Kelvin), ambient pressure (whatever the barometer reads) and saturated with water vapor with a partial pressure of 47 mm Hg at 37 degrees Centigrade. Conventionally, pulmonary physiologists express lung volumes such as vital capacity, inspiratory and expiratory capacity, residual lung volume and the dynamic measures of low lung function such as maximum breathing capacity at body temperature and moist, or BTPS. The following equation converts a gas volume ATPS to BTPS:

Gas volume BTPS =

$$V_{ATPS} \left( \frac{P_B - P_{H2O}}{P_B - 47 \text{ mm Hg}} \right) \left( \frac{310}{273 + T^\circ \text{ C.}} \right) \quad (5)$$

As the case with correction factors to STPD, appropriate BTPS correction factors are available for converting moist gas volume at ambient conditions to a volume BTPS.

In determining oxygen consumption in pulmonary function tests, the goal is to determine how much oxygen has been removed from the inspired air. Because the composition of inspired air remains relatively constant, it is possible to determine how much oxygen has been removed from the inspired air by measuring the amount and composition of the expired air. Normally, ambient air contains 0.03 percent $CO_2$, 20.93 percent $O_2$, and 79.04 percent $N_2$. When the air is expired from the individual being studied, the expired air contains more carbon dioxide (usually 2.5 percent to 5.0 percent), less oxygen (usually 15.0 percent to 18.5 percent) and more nitrogen (usually 79.04 percent to 79.60 percent). However, nitrogen is inert in terms of metabolism. Any change in nitrogen concentration in expired air reflects the fact that the number of oxygen molecules removed from the inspired air are not replaced by the same number of carbon dioxide molecules produced in metabolism. This results in the volume of expired air ($V_E$, STPD) being unequal to the inspired volume ($V_I$, STPD). For example, if the respiratory quotient is less than 1.0 (that is, less $CO_2$ produced in relation to $O_2$ consumed), and three liters of air are inspired, less than three liters of air will be expired. In this case, the nitrogen concentration is higher in the expired air than in the inspired air. That is not to say that nitrogen has been produced, only that nitrogen molecules now represent a larger percentage of $V_E$ as compared to $V_I$. In fact, $V_E$ differs from $V_I$ in direct proportion to the change in nitrogen concentration between the inspired and expired volumes. Thus, $V_I$ can be determined from $V_E$ using the relative change in nitrogen in an equation known as the Haldane transformation:

$$V_I \text{ STPD} = V_E \text{ STPD} \times \frac{\% N_{2E}}{\% N_{2I}} \quad (6)$$

where $N_{2I}$ percent equals 79.04 and $N_{2E}$ percent equals nitrogen in expired air computed from gas analysis as:

$$[(100 - (\%O_{2E} + \%CO_{2E})]$$

The volume of $O_2$ in the inspired air ($VO_{2I}$) can then be determined as follows:

$$VO_{2I} = V_I \times \%O_{2I} \quad (7)$$

Substituting equation (6) for $V_I$:

$$VO_{2I} = V_E \times \frac{\% N_{2E}}{79.04\%} \times \% O_{2I} \quad (8)$$

where $O_{2I}$ percent equals 20.93%.

The amount or volume of oxygen in the expired air ($VO_{2E}$) is computed as:

$$VO_{2E} = V_E \times \%O_{2E} \quad (9)$$

where $O_{2E}$ percent is the fractional concentration of oxygen in expired air determined by gas analysis.

The amount of $O_2$ removed from the inspired air each minute ($\dot{V}O_2$) can then be computed by the analyzer of the present invention as follows:

$$\dot{V}O_2 = (\dot{V}_I \times \%O_{2I}) - (\dot{V}_E \times \%O_{2E}) \quad (10)$$

By substitution:

$$\dot{V}O_2 = \left\{ \left| \left( \dot{V}_E \times \frac{\% N_{2E}}{79.04\%} \right) \times 20.93\% \right| - (\dot{V}_E \times \% O_{2E}) \right\} \quad (11)$$

where $\dot{V}O_2$ equals the volume of oxygen consumed per minute expressed in millimeters or liters and $V_E$ equals the expired air volume per minute expressed in millimeters or liters. Equations (11) can be simplified to:

$$\dot{V}O_2 = \dot{V}_E \left| \left( \frac{\% N_{2E}}{79.04\%} \times 20.93\% \right) - \% O_{2E} \right| \quad (12)$$

and the final form of the equation is:

$$\dot{V}O_2 = \dot{V}_E[(\%N_{2E} \times 0.265) - \%O_{2E}] \quad (13)$$

The value obtained within the brackets of equations (12) and (13) is referred to as the true $O_2$. This represents the "oxygen extraction" or, more precisely, the percentage of oxygen consumed for any volume of air expired.

Although equation (13) is the equation most widely used to compute oxygen consumption from measures of expired air, it is also possible to calculate the $VO_2$ from direct measurements of $V_I$ and $V_E$. In this case, the Haldane transformation is not used and oxygen consumption is calculated directly as:

$$\dot{V}O_2 = (\dot{V}_I \times 20.93) - (V_E \times \%O_{2E}) \quad (14)$$

In situations where only $V_I$ is measured, the $V_E$ can be calculated from the Haldane transformation as:

$$\dot{V}_E = \dot{V}_I \times \frac{\% N_{2I}}{\% N_{2E}}$$

By substitution into equation (14), the equation becomes:

$$\dot{V}O_2 = \dot{V}_I \left| \% O_{2I} - \left( \frac{\% N_{2I}}{\% N_{2E}} \times \% O_{2E} \right) \right| \quad (15)$$

The carbon dioxide production per minute $VCO_2$ is calculated as follows:

$$\dot{V}CO_2 = \dot{V}_E(\%CO_{2E} - \%CO_{2I}) \quad (16)$$

where $\%CO_{2E}$ equals percent carbon dioxide in expired air determined by gas analysis and $\%CO_{2I}$ equals percent carbon dioxide in inspired air which is essentially constant at 0.003%.

Thus, the final form of the equation is:

$$\dot{V}CO_2 = \dot{V}_E(\%CO_{2E} - 0.03\%) \quad (17)$$

This equation is used by the analyzer of the present invention to calculate carbon dioxide production.

The respiratory quotient (RQ) can be calculated one of two ways:

$$RQ = \dot{V}CO_2/\dot{V}O_2 \tag{18}$$

or $$RQ = \frac{(\% \ CO_{2E} - 0.03\%)}{\text{"true"} \ O_2} \tag{19}$$

Figure 15:
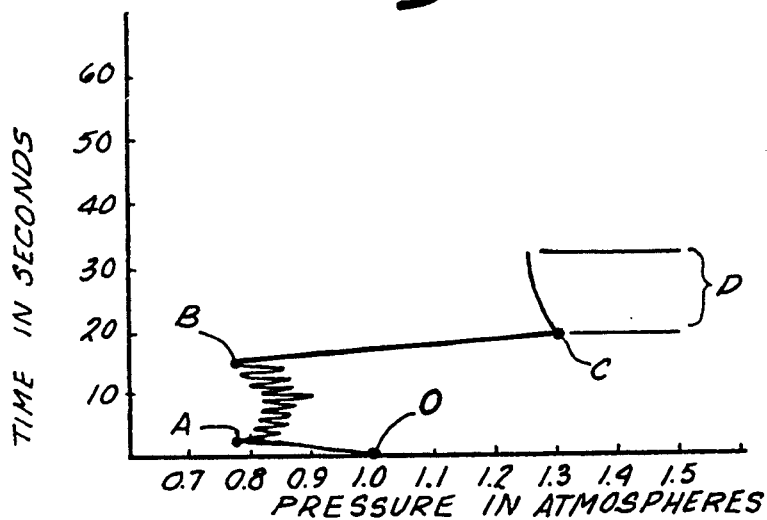
FIG. 15 is a plot of time versus pressure as measured by the pressure transducer in the metabolic rate analyzer of the present invention.

In determining the total expired volume at two inches of Hg vacuum, the flow proportioning valve of the present invention samples about 0.1 percent of the total flow of expired gas. Therefore, if the volume of the sample cylinder is 30 cc when it is fully charged, the total expired volume of gas from the individual equals 30 liters. However, as illustrated by the plot of FIG. 15, the vacuum supplied to the flow proportioning valve during the sample draw is not maintained at a constant level. Stiction between the sample cylinder and sample piston as well as flow losses and inertia cause the pressure to fluctuate as illustrated between points A and B of the plot of FIG. 15 against a pressure bias point. Therefore, it is necessary to correct the expired volume as follows:

$$V_E = \frac{KRV_s}{K'} \tag{20}$$

where K equals the assumed vacuum, K' equals the measured vacuum (mean), R equals a proportioning ratio, and $V_s$ equals the volume of the sample collected.

Thus, the analyzing means of the present invention converts the analog inputs for temperature, pressure and $O_2$ content into corresponding digital signals which are inputted to a programmed digital processor for determining the rate of pressure decay, correlating the same to a value for $CO_2$ content in the sample gas, conducting a volumetric analysis with temperature and pressure signals, and then correlating $CO_2$ content, $O_2$ content and volume to produce a measure of metabolic rate. The information is thus displayed along with other parameters of interest to the user, such as heart rate, respiration rate, time, the results of previous tests, differences between tests, etc., to provide a measure of various pulmonary and physiological functions. The analyzer thus also corrects for nonlinear outputs of the flow proportioning valve, corrects the volumetric analysis for actual vacuum sensed during the sample draw, and corrects $O_2$ output for actual sample pressure.

It should be understood that the gas analysis technique disclosed in the metabolic rate analyzer of the preferred embodiment may also have utility as a $CO_2$ monitor or a monitor for any one or number of gases in a mixture of gases to be analyzed. For example, a $CO_2$ gas analyzer for the art of capnography or any other application where a measure of $CO_2$ content is required, may comprise a test chamber, a means for drawing a representative sample of the gas mixture and then charging the sample into the test chamber, a pressure sensor and an analyzer. The sample cylinder and sample piston of the preferred embodiment of the present invention is suitable for such an application. A selectively-permeable membrane is disposed in the test chamber, the membrane being provided with a selective permeability for $CO_2$ (or any other gases of interest), the membrane being disposed in the test chamber for selectively venting $CO_2$ from the test chamber. The pressure sensor is provided for monitoring the pressure of the sample and determining the rate of pressure decay in the test chamber due to the selective venting of $CO_2$ through the selectively-permeable membrane. An analyzing means is provided for determining the $CO_2$ content (or the content of any other gases of interest) in the gas mixture being studied from the rate of pressure decay in the test chamber.

A temperature sensor may be provided for temperature compensating the analyzer and a multiple gas analysis may be conducted by providing multiple test chambers with membranes disposed therein for selectively venting other gases of interest. Such membranes may be dissimilar in composition or may be biased with a blocking agent, reference gas, liquid, or the like, to block the partial pressure driving force of any interfering gas contained within the sample to provide the desired differential permeability in the case of each gas of interest. Thus, it should be understood that the terms "selective permeability" as used herein have a somewhat broader meaning than that normally attributed to these terms. For example, even if the gas of interest in the analysis does not permeate through the membrane faster than other gases in the mixture, as long as there is a significant or measurable rate of permeability and the partial pressure driving the other gases is blocked, or the concentration of the other gases is known, there is said to be sufficient "selective" or "differential" permeability to solve for the gas of interest.

In an embodiment of the invention employing two sample chambers, one with ambient air as a reference, the other with sample gas as a reference, the simultaneous equations for calculating $CO_2$ content and $O_2$ content are developed as follows:

$$F = \frac{PrA(Pa - Pb)}{t} \tag{21}$$

where F equals flow (cc @25 degrees C×76 cm Hg/sec), t equals membrane thickness (∼0.0025 cm), Pr equals permeability (∼270×10⁻¹⁹ for $CO_2$ and ∼50×10⁻¹⁹ for $O_2$), A equals are (∼1 cm²) and (Pa−Pb) equals the partial pressure difference across the membrane in cm Hg of either $CO_2$ or $O_2$.

It can be determined that for an air reference at NTP that $CO_2$ flow equals:

$$FCO_2(\text{air}) = \frac{270 \times 10^{-9} \left(\frac{PiPCO_2}{76}\right)}{.0025} \tag{22}$$

or $$FCO_2(\text{air}) = 1.4P \ PiCO_2 \times 10^{-6}$$

and $O_2$ flow equals:

$$FO_2(\text{air}) = \frac{50 \times 10^{-9} \left(\frac{PiPO_2 - 15.6}{76}\right)}{.0025} \tag{23}$$

or $$FO_2(air) = \left( \frac{20 PiPO_2}{76} - 312 \right) 10^{-6}$$

where Pi equals the total sample pressure when the test chamber is charged with sample gas and it is assumed that $N_2$ flow is negligible differentially because its contribution to total flow can be ignored. Also, ambient air assumed to be 20.6 percent $O_2$. Total flow FT(air) for $O_2$ and $CO_2$ with an air reference then equals equation (22) plus equation (23):

$$FT(air) = (0.26 PiPO_2 + 1.4 PiPCO_2 - 312) 10^{-6} \quad (24)$$

Now, for a sample gas reference at NTP, $CO_2$ flow $FCO_2(sg)$ equals:

$$FCO_2(sg) = \frac{270 \times 10^{-9}}{.0025} \left( \frac{PiPCO_2}{76} - PCO_2 \right) \quad (25)$$

or $$FCO_2(sg) = 108 PCO_2 \left( \frac{Pi}{76} - 1 \right) 10^{-6}$$

and $O_2$ flow $FO_2(sg)$ equals:

$$FO_2(sg) = \frac{50 \times 10^{-9}}{.0025} \left( \frac{PiPO_2}{76} - PO_2 \right) \quad (26)$$

or $$FO_2(sg) = 20 PO_2 \left( \frac{Pi}{76} - 1 \right) 10^{-6}$$

total flow FT(sg) for $O_2$ and $CO_2$ with a sample reference equals equation (25) plus equation (26):

$$FT(sg) = (108 PCO_2 + 20 PO_2) \left( \frac{Pi}{76} - 1 \right) 10^{-6} \quad (27)$$

From Boyle's Law:

$$Pi(1 - T_e FT(air)) = Par \quad (28)$$

$$Pi(1 - T_e FT(sg)) = Psg \quad (29)$$

where $T_e$ equals the time elapsed during the pressure decay, Par equals the sample pressure at the end of this time for the test chamber with the air reference and Psg equals the sample pressure for the test chamber with the sample reference.

If the sample volume is assumed to be 1 cc, substituting into equation (28):

$$Pi[1 - T_e 10^{-6}(.26 PiPO_2 + 1.4 PiPCO_2 - 312)] = Par \quad (30)$$

and $$PCO_2 = \frac{10^{-6}}{1.4 T_e} \left(1 - \frac{Par}{Psg}\right) + 11.14 - .185 PiPO_2$$

Similarly, substituting into equation (29):

$$Pi\left[1 - T_e 10^{-6}\left(\frac{Pi}{76} - 1\right)(108 PCO_2 + 20 PO_2)\right] = Psg \quad (31)$$

and $$PCO_2 = \frac{10^{-6}(Pi - Psg)}{108 T_e Pi \left(\frac{Pi}{76} - 1\right)} - \frac{20 PO_2}{108}$$

Now substituting for $PCO_2$:

$$PO_2 = \frac{10^6}{.185(Pi - 1)} \left[ \frac{(1 - Par/Pi)}{1.4 T_e} - \right. \quad (32)$$

$$\left. \frac{(Pi - Psg)}{108 T_e Pi(Pi/760 - 1)} + \frac{11.14}{10^6} \right]$$

and alternately from equations (30) and (31), we obtain:

$$PO_2 = \frac{1}{.185 Pi} \left[ PCO_2 + \frac{10^6(1 - Par/Pi)}{1.4 T_e} + 11.4 \right] \quad (33)$$

$$PO_2 = \frac{1}{.185} \left[ \frac{10^6(Pi - Psg)}{108 T_e(Pi/76 - 1)} - PCO_2 \right] \quad (34)$$

$$PCO_2 = \frac{1}{(1/Pi + 1)} \left[ \frac{10^6(Pi - Psg)}{108 T_e(Pi/76 - 1)} - \right. \quad (35)$$

$$\left. \frac{10^6(1 - Par/Pi)}{1.4 T_e Pi} - \frac{11.4}{Pi} \right]$$

With reference now to FIGS. 1-4 and the graphs of FIGS. 15 and 16, the operation of the metabolic rate analyzer of the present invention will be described in further detail along with a method for analyzing metabolic rate and conducting a single or a multiple gas analysis for other gases of interest.

With specific reference now to FIG. 1, the metabolic rate analyzer of the present invention is illustrated at the point in the system operation where the system is poised for a sample draw. This position corresponds to position O in the plot of FIG. 15 which plots time against system pressure in atmospheres. As illustrated in FIG. 15 at position O purged, the pressure in the system is equal to 1.0 atmosphere. To reach this condition, the crank shaft wheel 90 is rotated clockwise from the analyze position illustrated in FIG. 4 to the position illustrated in FIG. 1. During this clockwise rotation of the crank shaft wheel 90, the drive pawl 120 engages the rest pawl 119, sequence valve 101 and vent valve 103 are momentarily opened (second sequence valve 102 is already opened) to flush the system, and then second sequence valve 102 is closed, resulting in the system configuration illustrated in FIG. 1, poised for a sample draw. The draw of sample gas is then initiated by releasing the hand crank 91 to allow the torsion spring to rotate the crank shaft wheel 90 counterclockwise, withdrawing the sample piston 15 from the sample cylinder 14 to conduct the sample draw. The system is now in position A in the plot of time and pressure of FIG. 15. As the sample piston 15 is drawn from the sample cylinder 14, a vacuum is pulled in the sample cylinder 14. This vacuum is maintained in the sample cylinder until and unless the subject being studied discharges expired gas into the flow proportioning valve 10. The discharge of expired gas into the flow proportioning valve 10 displaces the flexible diaphragm of the flow proportioning valve, creating a corresponding and proportional displacement in the pintle valve contained therein so that a proportional sample of the expired gas of the subject being studied is drawn into the sample cylinder 14 in the direction of the arrows 180 illustrated in FIG. 1. Repeated discharges of expired gas from the subject will eventually fill the sample chamber with a representative and proportional sample of the expired gases of the subject. This cyclical respiratory activity will provide for some pressure fluctuation within the sample cylinder 14 and produces the periodic wave form illustrated in FIG. 15, which extends from point A to point B in FIG. 15. The periodic wave form illustrated in FIG. 15 between points A and B may be analyzed to provide a measure of respiratory rate. Point B in FIG. 15 represents the point a which the sample cylinder 14 is substantially full of a proportional sample of the expired gas and the system is ready to purge and charge the test chamber 16.

Figure 2:
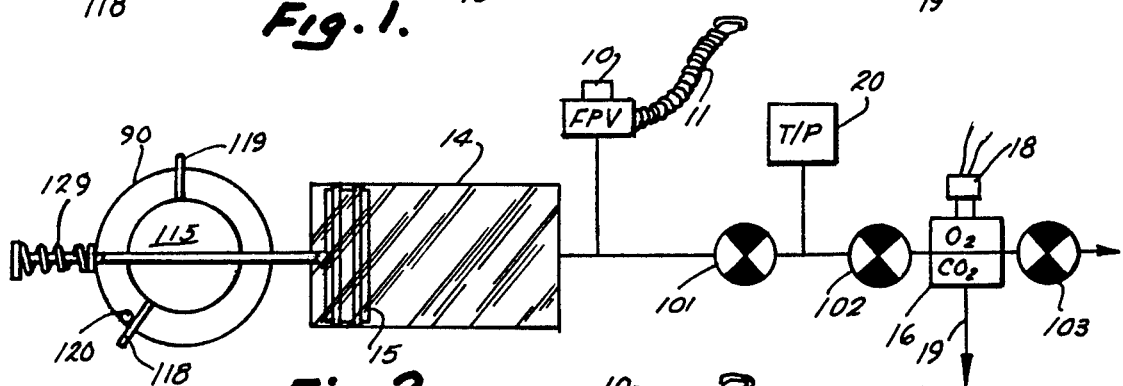
FIG. 2 is a schematic illustration of the metabolic rate analyzer of FIG. 1 with the system, having drawn a sample, now poised to purge.

In FIG. 2, the system is illustrated poised to purge the test chamber 16. To reach this position, the crank shaft wheel 90 rotates counterclockwise because of torque applied by torsionally loaded coil spring 122, whenever the subject discharges expired air into flow proportioning valve 10, until it approaches bottom dead center (BDC) of the sample piston 15. After a number of respiratory cycles, the reciprocating carrier 83 comes to a stop on the spring loaded resilient stop 127. The system may be permitted to dwell in this position indefinitely or until the user decides it is appropriate to complete the purge, charge and analyze portions of the operating cycle. The system can dwell after the sample draw because the sample is isolated in the sample cylinder and the second sequence valve 102 is still closed.

To begin the purge portion of the operating cycle illustrated in FIG. 2, the user manually rotates the hand crank 91, turning the crank shaft wheel 90 counterclockwise, compressing the spring loaded resilient stop 127, and driving the sample pawl 118 with the drive pawl 120. As the sample piston passes BDC and is displaced back into the sample cylinder, displacement of the rotatable cam plate 115 initiates the purge portion of the operating cycle by opening second sequence valve 102. The purge and charge portions of the cycle are continued by further manual counterclockwise rotation of the crank shaft wheel 90. In the purge portion of the cycle, further counterclockwise rotation of the crank shaft wheel 90 displaces the sample piston into the sample cylinder, driving sample gas through the test chamber 16 and out the vent valve 103. The vent valve 103 is not closed until the beginning of the charge portion of cycle when it is necessary to compress and isolate a portion of the sample in the test chamber 16.

Figure 3:
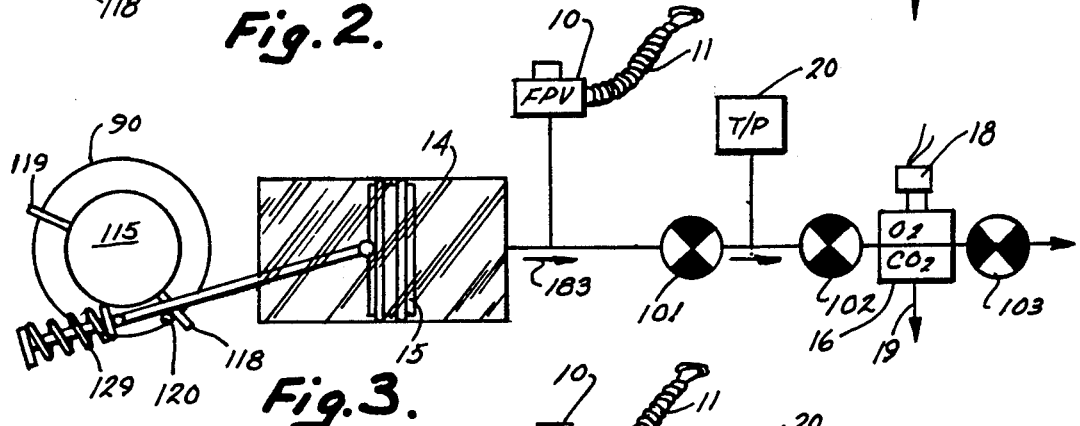
FIG. 3 is a schematic illustration of the metabolic rate analyzer of FIG. 1 with the system poised to charge the test chamber.

With reference now to FIG. 3, at the beginning of the charge portion of the cycle, the first sequence valve 101 is open to admit the pressurized sample gas to the test chamber 16. The second sequence valve 102 is open to admit sample gas to the test chamber 16 and the vent valve 103 is closed to isolate the test chamber 16 from the atmosphere. The sequence valves 101 and 102 are already open in the purge, so the charge is started by further manual rotation of the crankshaft wheel 90 counterclockwise to displace the cam plate 115 to close vent valve 103. During the charge portion of the operating cycle, the sample piston 15 is further displaced manually into the sample chamber 14 in the direction of the arrow 182 to pressurize the sample gas contained therein and drive the same into the test chamber in the direction of the arrows 183 under pressure. Flow is prevented from returning to the flow proportioning valve 10 by the seating action of the needle-shaped valve spindle 58. Thus, the only path for the sample gas is into the test chamber 16. The force for pressurizing the test chamber 16 comes from the torsional loading of the coil spring disposed about the central crank shaft 107, combined with manual actuation of the hand crank 91. The pressure applied to test chamber 16 is limited, as described above, by the setting of compression spring 129 on the connecting rod. At the beginning of the purge cycle of the metabolic rate analyzer, the system is at position B in the time versus pressure plot of FIG. 15. As the crank shaft is displaced and the system is pressurized, pressure rises to point C in the plot of FIG. 15, where it is illustrated that the sample chamber 16 is raised to a pressure substantially greater than one atmosphere.

Figure 4:
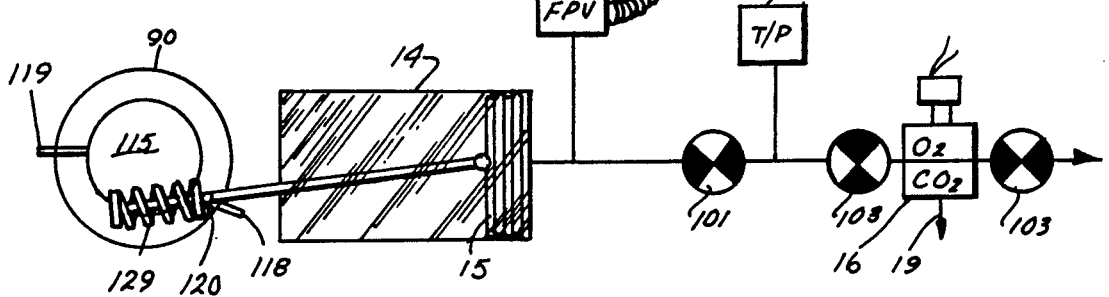
FIG. 4 is a schematic illustration of the metabolic rate analyzer of FIG. 1 with the system disposed in an analyze position.

With reference now to FIG. 4, the system is illustrated in the analyze portion of the operating cycle. The analyze portion of the operating cycle begins when the sample chamber 16 is charged and further manual actuation of the crank shaft wheel 90 and cam plate 15 closes the first sequence valve 101, isolating a pressurized sample in the sample chamber 16. Closure of the first sequence valve 101 isolates the temperature/pressure sensor 20 and the test chamber 16 from the sample cylinder 14. With the test chamber 16 thus charged with a mixture of gas which includes the gases of interest, the galvanic oxygen sensor 18 provides a measure of $O_2$ content in the sample and the pressure sensor 20 provides a measure of the rate of pressure decay in the test chamber 16 due to the selective venting of $CO_2$ through the membrane having a selective permeability for $CO_2$. Even if the sample chamber 16 is charged with air, the pressure in the test chamber 16 will decay with time because of the permeability of the various constituent gases contained within air through the membrane in the test chamber 16. However, because the membrane disposed in the test chamber 16 is provided with a selective permeability for $CO_2$ or a differential permeability rate for $CO_2$ that is large compared to the permeability rate for other gases in air, or at least which is significant when compared to other permeability rates, the time rate of change for pressure in the test chamber 16 for various concentrations of air and $CO_2$ can be determined. As $CO_2$ is selectively and preferentially vented from the test chamber 16 in the direction of the arrow 19, the pressure in the test chamber 16 will decay as indicated by the portion of the plot of FIG. 15 labeled D.

Figure 16:
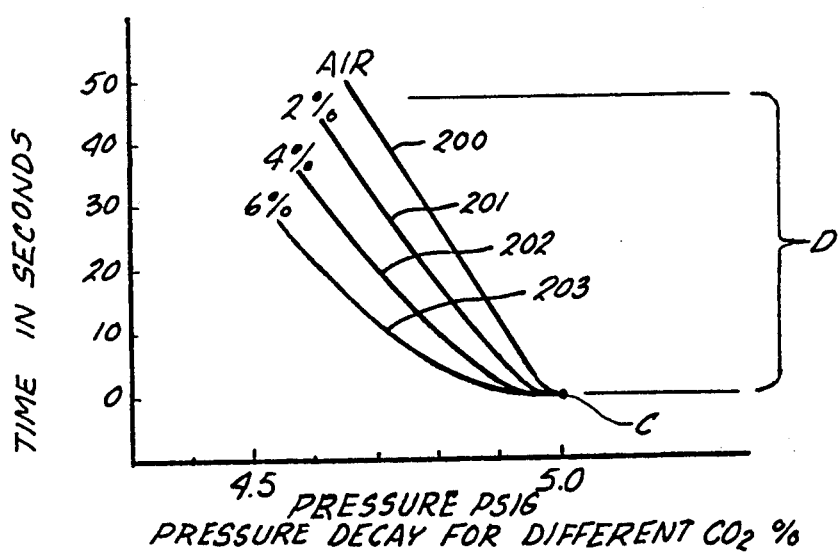
FIG. 16 is a plot of time versus pressure during the analyze portion of the operational cycle of the metabolic rate analyzer of the present invention when pressure decay in the test chamber is analyzed.

Now with particular reference to FIG. 16, which is an enlarged plot of section D of FIG. 15, it is illustrated that decay rates for pressure in the test chamber 16 will vary according to the concentration of $CO_2$ in the sample gas. The decay rate for standard air is illustrated at 200. Since standard air does not have an enriched $CO_2$ content, the pressure decay for air is fairly linear. However, at two percent, four percent and six percent $CO_2$ contents, as plotted in curves 201, 202 and 203, respectively, it is illustrated that the initial slopes of all such decay curves increase significantly with very small increases in the concentration of $CO_2$ in the sample gas. It should be readily apparent that the slopes of all such curves gradually approach that of air as the $CO_2$ in the sample gas is the first to be selectively vented from the test chamber. Therefore, the portion of the curve which merits attention is the very first few seconds after the pressurization of the test chamber 16. It is possible to provide a very accurate measure of the $CO_2$ concentration in the sample gas by measuring the pressure in the test chamber at the end of a given analyzing period and then comparing that pressure to the highest pressure sensed during the charging of the test chamber. This measure of pressure decay or pressure drop during a known analyzing period will provide a direct measure of the $CO_2$ content in the sample gas. Such a measure can be provided by simply plotting the pressure decay in the test chamber for providing a measure of the total pressure decay within a given time period.

However, in the preferred embodiment of the invention, the temperature, pressure and $O_2$ signals are converted to digital representations which are inputted to a programmed digital processor which compensates for sample temperature; conducts a volumetric analysis of the proportional sample to provide a measure of the total volume of gas expired from the subject being studied; determines the rate of pressure decay in the test chamber by, for example, measuring the slope of the decay curve at a point near the beginning of the analyzing portion of the operational cycle; and then correlates $O_2$ content, $CO_2$ content and total volume of expired gas to provide a measure of the metabolic rate of the subject being studied.

Figure 18:
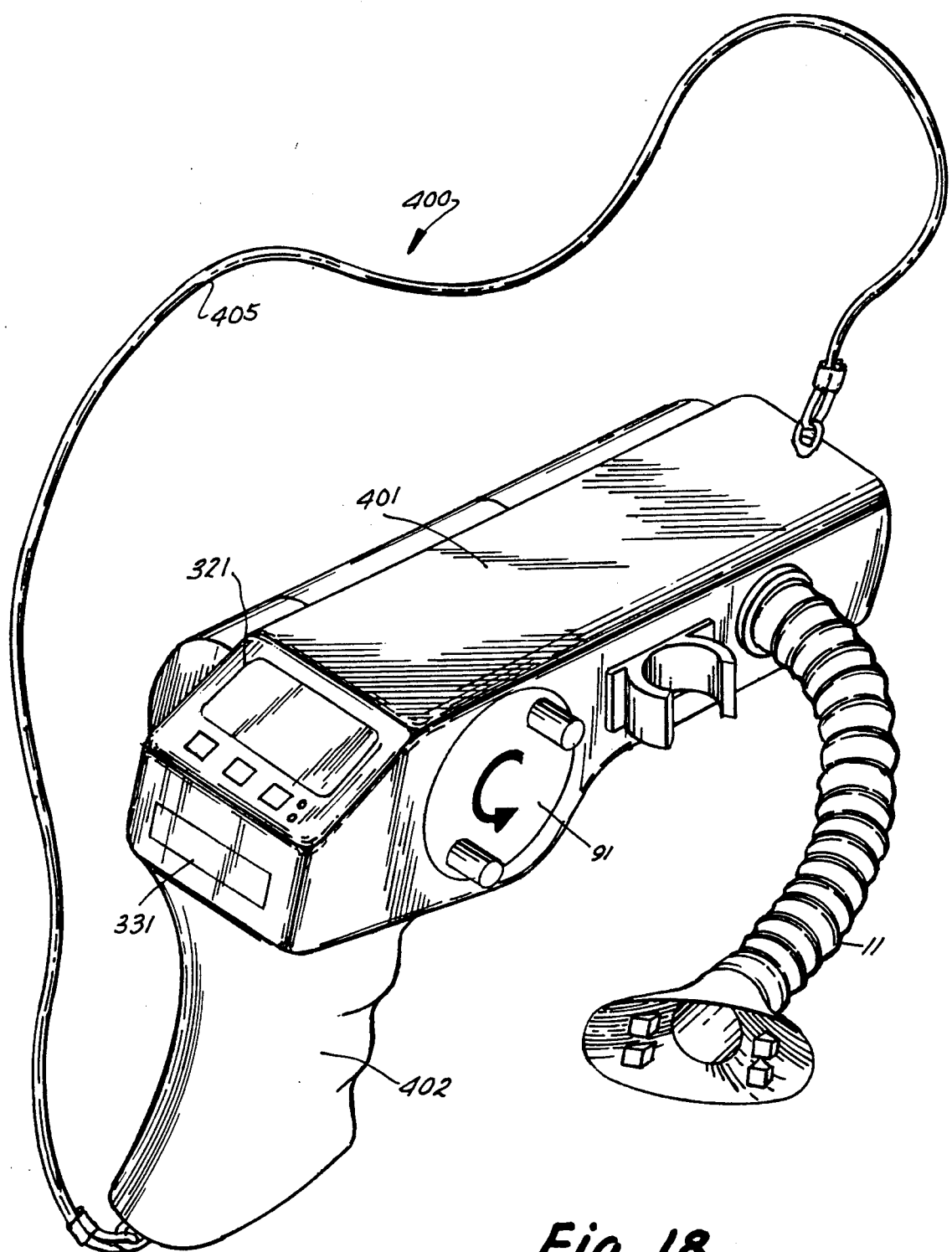
FIG. 18 is a perspective view of one embodiment of the metabolic rate analyzer of the present invention that is suitable for mounting in a holster or sling that ma be carried with an athlete for monitoring the metabolic rate of the athlete during vigorous exercise.

With reference now to FIG. 18, one embodiment of the metabolic rate analyzer of the present invention is generally illustrated at 400. In this case, the metabolic rate analyzer 400 is embodied in an elongate body 401 with a pistol grip 402 disposed thereon. The analyzer 400 can be carried by an individual using the sling 405 or placing the body 401 of the analyzer in a holster or the like which is strapped to the user's body. The mouthpiece and flexible hose 11 projects from one end of the body 401 and the hand crank 91 is centrally located on the body 401. The RS-232 port is illustrated at 331 and the display and user interface is illustrated at 321.

Figure 19:
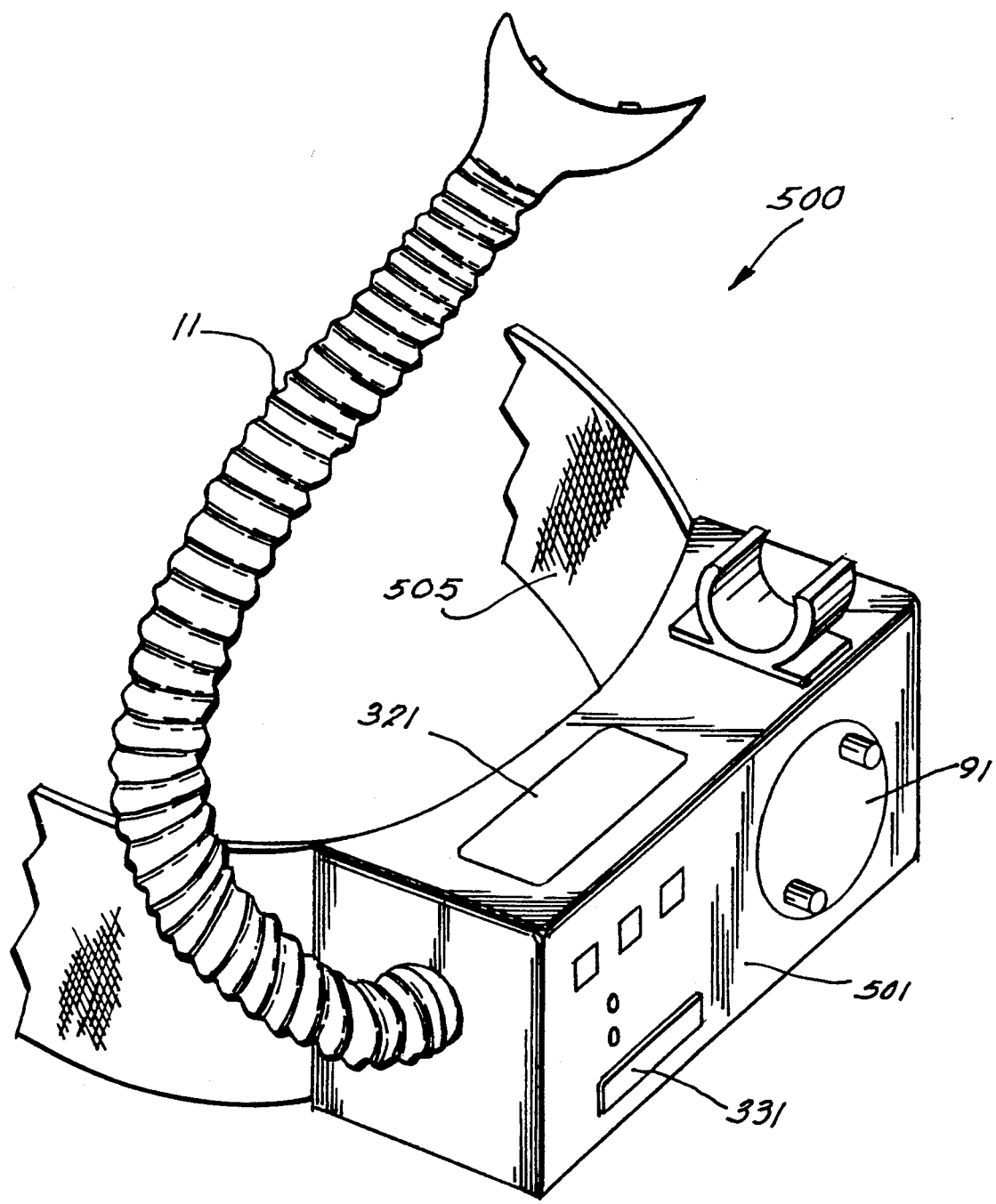
FIG. 19 is a perspective view of one embodiment of the metabolic rate analyzer of the present invention that is suitable for mounting about the waist or chest of an athlete for monitoring the metabolic rate of the athlete during vigorous exercise.

With reference now to FIG. 19, another embodiment of the invention is generally illustrated at 500. In the embodiment of the invention illustrated in FIG. 19, the analyzer is disposed in an elongate body 501 which includes belt loops or the like for receiving a strap 505 which extends around the waist or chest of the user. The flexible hose and mouthpiece is illustrated at 11, the hand crank is illustrated at 91, the display panel is at 321 and the RS-232 port is disposed at 331. It should be noted that with the simple mouthpieces illustrated in FIGS. 18 and 19, a nose clip is not provided. Thus, to ensure the accuracy of the test, the user will be forced to clamp his nose to close nasal passages when discharging expired air into the analyzer. Alternately, a nose clip can be provided with the instrument to be used in conjunction with the mouthpiece, or the mouthpiece can be replaced with a mask that covers both the mouth and nasal passages.

It should be understood that the test chamber and sample cylinder of the present invention could be used to conduct a single gas analysis such as a $CO_2$ gas analysis of the type required in the art of capnography. Further, it should be understood that multiple samples could be taken in parallel as previously described with regard to the embodiment of FIG. 5 to conduct simultaneous multipath gas analysis on a sample of a mixture of gases where there were multiple gases of interest. The membranes in the various analyzer paths that may be provided in such a system configuration may comprise dissimilar membranes or may involve similar membranes with different reference gases on the low pressure side of the membrane.

In the preferred embodiment of the metabolic rate analyzer of the present invention, a discrete $O_2$ sensor is used because such sensors are an accurate, simple, and relatively inexpensive expedient. However, no such accurate, simple, inexpensive expedients exist for $CO_2$ analysis. The best approach for conducting $CO_2$ analysis in the prior art is the non-dispersive IR gas analysis technique described in the Background Of The Invention.

In applications of the invention that are not required to be portable, it may be desirable to replace the hand crank, torsion spring and much of the other mechanical disclosure contained herein with an electric motor, solenoids, solenoid-activated valves, a motor driven pump or the like. Such applications may include, for example, bedside monitors used in cardiac rehabilitation or monitors incorporated in stationary exercise machines such as treadmills, stationary bicycles, stair machines, or the like. In any of these applications, other available inputs may be processed by the analyzer, such as heart rate and blood pressure. These other inputs may then be correlated with $O_2$ consumed, $CO_2$ produced and respiratory volume to refine the analysis of metabolic rate and provide other measures of physical performance or conditioning.

The above description is exemplary and should be considered that of the preferred embodiment only. Modifications will occur to those skilled in the art who make and use the invention. It is desired to include within the scope of the present invention all such modifications of the invention that come within the proper scope of the appended claims.

The embodiments of the invention in which an exclusive property or privilege is claimed are defined as follows:

1. A metabolic rate analyzer comprising:
   a flow proportioning valve for producing a proportional sample of the expired gas of a subject being studied;
   a means for drawing from said flow proportioning valve a proportional sample of the expired gas of the subject;
   a test chamber;
   an $O_2$ sensor;
   a selectively-permeable membrane disposed in said test chamber, said membrane being provided with a selective permeability for $CO_2$, said membrane being disposed in said test chamber for selectively venting $CO_2$ from said test chamber;
   a means for charging said test chamber with the proportional sample of the expired gas of the subject;
   a pressure sensor for monitoring the pressure of the sample and determining the rate of pressure decay in said test chamber due to the selective venting of $CO_2$ through said selectively-permeable membrane; and
   an analyzing means for determining the $CO_2$ content of the expired gas of the subject from the rate of pressure decay in said test chamber, for conducting a volumetric analysis of the proportional sample to determine the total volume of gas expired from the subject being studied, and correlating $O_2$ content, $CO_2$ content and total volume of expired gas to provide a measure of the metabolic rate of the subject being studied.

2. The metabolic rate analyzer of claim 1 further comprising a temperature sensor for monitoring the temperature of the sample, and said analyzing means further comprising means for determining $CO_2$ content and conducting volumetric analysis corrected for sample temperature.

3. The metabolic rate analyzer of claim 1 wherein said analyzing means further comprises means for correcting the output of said $O_2$ sensor according to the pressure in said test chamber.

4. The metabolic rate analyzer of claim 1 wherein said analyzing means further comprises means for correcting the volumetric analysis according to the pressure actually sensed when drawing a proportional sample of the expired gas of the subject being studied.

5. The metabolic rate analyzer of claim 1 wherein said $O_2$ sensor comprises:
an oxygen test chamber;
a second membrane disposed in said oxygen test chamber, said second membrane being provided with a permeability for $O_2$, said second membrane being disposed in said oxygen test chamber for venting $O_2$ from said oxygen test chamber;
a means for charging said oxygen test chamber with the proportional sample of the expired gas of the subject;
an oxygen pressure sensor for monitoring the pressure of the sample in said oxygen test chamber and determining the rate of pressure decay in said oxygen test chamber due to the venting of $O_2$ through said oxygen membrane; and
a means for determining the $O_2$ content of the expired gas of the subject from the rate of pressure decay in said oxygen test chamber.

6. The metabolic rate analyzer of claim 5 wherein said second membrane is similar in composition to said membrane having a selective permeability for $CO_2$ and different reference gases are provided for both of said membranes.

7. The metabolic rate analyzer of claim 6 wherein a reference gas of ambient air is provided for said membrane having a selective permeability for $CO_2$.

8. The metabolic rate analyzer of claim 7 wherein a reference gas comprising a sample of the expired gas of the subject being studied is provided for said second membrane.

9. The metabolic rate analyzer of claim 1 wherein said flow proportioning valve comprises a diaphragm actuated by the expired gas of the subject being studied; and a pintle valve actuated by displacement of said diaphragm, the output of said pintle valve being connected to said means for drawing.

10. The metabolic rate analyzer of claim 9 wherein said pintle valve comprises a valve body; a generally cylindrical bore disposed in said valve body; and a needle-shaped valve spindle generally cylindrical in cross section, disposed in said generally cylindrical bore.

11. The metabolic rate analyzer of claim 10 wherein said generally cylindrical bore is provided with a proximate end and a distal end, said valve spindle being inserted in the proximate end of said bore and extending colinearly with said bore.

12. The metabolic rate analyzer of claim 11 wherein said pintle valve further comprises a positive shut-off valve.

13. The metabolic rate analyzer of claim 12 wherein said shut-off valve comprises an output passage disposed in said distal end of said bore; an elastomeric seat disposed in said distal end of said bore, said elastomeric seat surrounding said output passage; a blunt sealing surface disposed on an end of said needle-shaped valve spindle; and means for spring biasing said blunt sealing surface into engagement with said elastomeric seat.

14. The metabolic rate analyzer of claim 11 wherein said bore is provided with a right circular, constant, cross section and said needle-shaped valve spindle is provided with a guide portion of right circular cross section that is smaller than the right circular cross section of said bore, whereby a sliding fit is established between said bore and said spindle.

15. The metabolic rate analyzer of claim 14 wherein said needle-shaped valve spindle is provided with a meter portion of conical cross section, said meter portion being disposed between said guide portion and an end of said needle-shaped valve spindle.

16. The metabolic rate analyzer of claim 15 wherein said meter portion of said valve spindle is provided with a generally constant taper of one-half degree providing a cross section substantially identical to said guide portion of said valve spindle adjacent said guide portion and providing a substantially smaller cross section adjacent an end of said valve spindle.

17. The metabolic rate analyzer of claim 16 wherein said distal end of said bore is provided with a nominal diameter of about 0.070 inch.

18. The metabolic rate analyzer of claim 9 wherein said diaphragm is suspended in a valve housing which is bifurcated into an inlet manifold and an outlet manifold by a manifold wall.

19. The metabolic rate analyzer of claim 18 wherein said inlet manifold is provided with an inspired gas inlet comprising at least one inlet aperture covered by a one-way flap valve for admitting inspired air only.

20. The metabolic rate analyzer of claim 19 wherein said outlet manifold is provided with an expired gas main outlet.

21. The metabolic rate analyzer of claim 20 wherein said inlet manifold is provided with a breath port through which the inspired and expired gas of the subject being studied passes.

22. The metabolic rate analyzer of claim 21 wherein said manifold wall is provided with an expired gas outlet port which is normally covered and closed by said diaphragm.

23. The metabolic rate analyzer of claim 22 further comprising means for spring biasing said diaphragm, said means for spring biasing said diaphragm urging said diaphragm in a direction covering and closing said expired gas outlet port.

24. The metabolic rate analyzer of claim 23 further comprising an inlet for said pintle valve disposed in said inlet manifold.

25. The metabolic rate analyzer of claim 24 further comprising link means for connecting said diaphragm and said pintle valve and actuating said pintle valve, whereby displacement of said diaphragm, against said means for spring biasing said diaphragm, due to pressure from expired gas entering said inlet manifold through said breath port, opens said expired gas port providing for the discharge of expired gas into said outlet manifold while simultaneously and proportionally opening said pintle valve to provide a representative sample of the expired gas in said inlet manifold to said means for drawing.

26. The metabolic rate analyzer of claim 1 wherein said means for drawing comprises a sample cylinder and a sample piston, said sample piston being disposed within said sample cylinder and being in sliding, sealing engagement with said sample cylinder.

27. The metabolic rate analyzer of claim 26 wherein said flow proportioning valve further comprises a one-way check valve, whereby a proportional sample of the expired as of the subject is drawn from said flow proportioning valve by displacement of said sample piston out of said sample cylinder and said sample of the expired gas cannot be directed back through said flow proportioning valve by displacement of said sample piston into said sample cylinder.

28. The metabolic rate analyzer of claim 27 wherein said means for charging said test chamber with the proportional sample of the expired gas of the subject comprises said sample cylinder and said sample piston, said sample piston being displaced into said sample cylinder for pressurizing the sample and charging said test chamber.

29. The metabolic rate analyzer of claim 28 further comprising a first sequence valve interconnecting said sample cylinder and said pressure sensor, said first sequence valve being open when the sample is drawn to provide for pressure monitoring during the sample draw, said first sequence valve being open for directing the sample to said test chamber when said test chamber is charged, and said first sequence valve being closed during analysis for isolating said test chamber while monitoring pressure decay in said test chamber.

30. The metabolic rate analyzer of claim 29 further comprising a second sequence valve interconnecting said pressure sensor and said test chamber, said second sequence valve being closed when the sample is drawn for isolating said sample cylinder and said flow proportioning valve from said test chamber during the sample draw, said second sequence valve being open when said test chamber is purged and said test chamber is charged for directing the sample to said test chamber, and said second sequence valve remaining open during analysis to provide for the monitoring of pressure decay in said test chamber.

31. The metabolic rate analyzer of claim 30 further comprising a vent valve for connecting said test chamber to a vent, said vent valve being open when the sample is drawn and said test chamber is purged, said vent valve being closed when said test chamber is charged and said vent valve remaining closed during analysis for isolating said test chamber while monitoring pressure decay in said test chamber.

32. The metabolic rate analyzer of claim 31 further comprising a hand crank and a connecting rod means for interconnecting said hand crank and said sample piston.

33. The metabolic rate analyzer of claim 32 further comprising a crank shaft disposed on said hand crank and a torsional coil spring disposed about said crank shaft for driving said sample piston in a reciprocal motion in said sample cylinder when the sample is drawn and the test chamber is charged.

34. The metabolic rate analyzer of claim 33 further comprising a stationary valve assembly disposed about said crank shaft, said valve assembly including said first sequence valve, said second sequence valve and said vent valve.

35. The metabolic rate analyzer of claim 34 further comprising a rotary cam assembly disposed about said crank shaft, said cam assembly providing for the sequential actuation of said first sequence valve, said second sequence valve and said vent valve, said rotary cam assembly being driven by said crank shaft.

36. The metabolic rate analyzer of claim 35 wherein each of said first sequence valve, said second sequence valve and said vent valve comprise a length of flexible elastomer tubing extending through said stationary valve assembly; an actuator bore extending in a direction generally orthogonal to the direction of said tubing; and a ball actuator disposed for reciprocal motion in said actuator bore, said actuator bore intersecting said tubing, said ball actuator being in an abutting relationship with said tubing, said ball actuator being biased upwardly away from said elastomer tubing such that said ball actuator extends above said actuator bore, whereby said actuator ball is engaged by a cam surface disposed on said rotary cam assembly for camming said ball actuator down into said elastomer tubing and clamping the same closed.

37. The metabolic rate analyzer of claim 36 wherein a plurality of ball actuators are disposed in a circular array, and said cam surface on said rotary cam assembly comprises a flat portion for depressing said ball actuators and a circular track of circular cross section for releasing said ball actuators.

38. The metabolic rate analyzer of claim 36 wherein said rotary cam assembly is driven in one direction, when the sample is drawn and the sample chamber is charged, by a crank shaft pawl which engages a sample pawl disposed on said rotary cam assembly; and said rotary cam assembly is driven in another direction, to flush and reset the system for another sample draw, when said crank shaft pawl engages a reset pawl disposed on said rotary cam assembly.

39. The metabolic rate analyzer of claim 38 wherein said hand crank is provided for turning said crank shaft and loading said torsional coil spring, torque from said torsional coil spring thereafter displacing said sample piston for sample draw, sample draw continuing until said connecting rod means engages a resilient spring loaded stop defining the end of the sample draw, further manual displacement of said hand crank compressing said resilient spring loaded stop for displacing said sample piston beyond bottom dead center and continuing with the purge and sample charge.

40. The metabolic rate analyzer of claim 29 wherein said connecting rod means further comprises a pivotable connecting rod connected for pivotal and reciprocal motion to said hand crank.

41. The metabolic rate analyzer of claim 40 wherein said connecting rod means further comprises a sliding carrier mounted for reciprocal, linear movement on the metabolic rate analyzer, said sliding carrier engaging said spring loaded stop defining the end of the sample draw, and said pivotal connecting rod being pivotally mounted on said sliding carrier with a cylindrical bushing.

42. The metabolic rate analyzer of claim 41 wherein said connecting rod means further comprises a linear connecting rod mounted for linear displacement with said sliding carrier, said second connecting rod engaging said sample piston for displacing the same relative to said sample chamber.

43. The metabolic rate analyzer of claim 41 wherein said connecting rod means further comprises a compression loaded coil spring disposed between one end of said pivotal connecting rod and said sliding carrier, said pivotal connecting rod being slidably mounted in said cylindrical bushing, whereby the charge pressure of said test chamber is limited to a pressure related to the compression load on said compression loaded coil spring, displacement of said sample piston by said hand crank compressing the sample until the compression preload of said compression loaded coil spring is overcome, providing for displacement of said pivotal connecting rod relative to said sliding carrier upon further rotation of said hand crank, during the sample charge.

44. The metabolic rate analyzer of claim 1 wherein said test chamber comprises a pressure vessel; a sample outlet; a sample inlet; a sample window; a first porous sintered metal plate disposed in said sample window; a second porous sintered metal plate disposed in said sample window, said selectively-permeable membrane being disposed between said first and second sintered metal plates and supported by the same.

45. The metabolic rate analyzer of claim 1 wherein said selectively-permeable membrane comprises a silicone rubber membrane.

46. The metabolic rate analyzer of claim 45 further comprising a well disposed adjacent said selectively-permeable membrane, said well being disposed outside of said test chamber, said well containing a matrix saturated with water to compensate for the presence of water vapor in the sample gas.

47. The metabolic rate analyzer of claim 1 wherein said $O_2$ sensor is disposed in said test chamber and said $O_2$ sensor comprises a galvanic oxygen sensor.

48. The metabolic rate analyzer of claim 1 wherein said analyzing means further comprises a plurality of analog to digital converters for transforming analog signals representative of pressure and $O_2$ content into corresponding digital signals.

49. The metabolic rate analyzer of claim 39 wherein said analyzing means further comprises a programmed digital processor for determining the rate of pressure decay; correlating the same to a value for $CO_2$ content; conducting a volumetric analysis with pressure and system constants; and correlating $CO_2$ content, $O_2$ content and volume to produce a measure of metabolic rate.

50. A method for determining metabolic rate comprising the steps of:
producing a proportional sample of the expired gas of a subject being studied;
providing an $O_2$ sensor;
providing a test chamber with a pressure sensor and a selectively-permeable membrane, the membrane being provided with a selective permeability for $CO_2$, the membrane disposed in the chamber for selectively venting $CO_2$ from the test chamber;
charging the test chamber with the proportional sample of the expired gas of the subject being studied;
determining the $O_2$ content in the sample of expired gas with the $O_2$ sensor;
monitoring the pressure of the sample of the expired gas in the test chamber;
determining the rate of pressure decay in the test chamber due to the selective venting of $CO_2$ through the selectively-permeable membrane;
determining the $CO_2$ content of the sample of expired gas from the rate of pressure decay in the test chamber;
conducting a volumetric analysis of the proportional sample to provide a measure of the total volume of gas expired from the subject being studied; and
correlating $O_2$ content, $CO_2$ content and total volume of expired gas to provide a measure of the metabolic rate of the subject being studied.

51. The method of claim 50 wherein said analyzing step further comprises the step of correcting the volumetric analysis according to the pressure actually sensed during said step of producing a proportional sample.

52. The method of claim 50 wherein said analyzing step further comprises the step of correcting the $O_2$ sensor for actual pressure sensed during said analyzing step.

53. The method for determining metabolic rate of claim 73 wherein:
said step of providing an $O_2$ sensor comprises providing an oxygen test chamber with an oxygen pressure sensor and a second membrane having a permeability for $O_2$;
charging the oxygen test chamber with the proportional sample of the expired gas of the subject being examined;
monitoring the pressure of the sample of expired gas in the oxygen test chamber;
determining the rate of pressure decay in the oxygen test chamber due to the selective venting of $O_2$ through the oxygen membrane; and
determining the $O_2$ content of the sample of expired gas from the rate of pressure decay in the oxygen test chamber.

54. The method of claim 50 further comprising the steps of:
providing membranes of similar composition; and
providing different reference gases for each membrane.

55. The method of claim 50 further comprising the providing an ambient air reference for the membrane having a selective permeability for $CO_2$; and
providing a sample gas reference for the second membrane.

56. The method for determining metabolic rate of claim 50 further comprising the steps of:
providing a temperature sensor;
monitoring the temperature of the sample gas; and
temperature correcting the steps of monitoring pressure, determining rate of pressure decay, determining $CO_2$ content, conducting volumetric analysis and correlating $O_2$, $CO_2$ and volume to provide a measure of metabolic rate.

57. The method for determining metabolic rate of claim 50 further comprising the steps of:
forming a selectively-permeable membrane from silicone rubber; and
compensating for water vapor in the sample by saturating the outside surface of the silicone membrane with water.

* * * * *